US012527904B2

(12) United States Patent
Pratt et al.

(10) Patent No.: US 12,527,904 B2
(45) Date of Patent: Jan. 20, 2026

(54) TWO-PIECE DRESSING INCLUDING SWITCHABLE ADHESIVE

(71) Applicant: KCI Manufacturing Unlimited Company, Athlone (IE)

(72) Inventors: Benjamin Andrew Pratt, Poole (GB); Christopher Brian Locke, Bournemouth (GB); Justin Alexander Long, Lago Vista, TX (US)

(73) Assignee: KCI Manufacturing Unlimited Company, Westmeath (IE)

( * ) Notice: Subject to any disclaimer, the term of this patent is extended or adjusted under 35 U.S.C. 154(b) by 454 days.

(21) Appl. No.: 17/767,382

(22) PCT Filed: Oct. 15, 2020

(86) PCT No.: PCT/IB2020/059724

§ 371 (c)(1),
(2) Date: Apr. 7, 2022

(87) PCT Pub. No.: WO2021/079241

PCT Pub. Date: Apr. 29, 2021

(65) Prior Publication Data

US 2024/0075198 A1 Mar. 7, 2024

Related U.S. Application Data

(60) Provisional application No. 62/924,950, filed on Oct. 23, 2019.

(51) Int. Cl.
*A61M 1/00* (2006.01)
*A61F 13/0246* (2024.01)
(Continued)

(52) U.S. Cl.
CPC ......... *A61M 1/912* (2021.05); *A61F 13/0253* (2013.01); *A61F 13/05* (2024.01);
(Continued)

(58) Field of Classification Search
CPC .. A61F 13/0246; A61F 13/0253; A61F 13/05; A61F 5/443; A61F 2013/00655;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Stouch Lighting, Nov. 30, 2017, Everything You Need to Know About LED Lighting.*
(Continued)

*Primary Examiner* — Alireza Nia
*Assistant Examiner* — Andrew Jun-Wai Mok

(57) ABSTRACT

This disclosure describes devices, systems, and methods related to two-piece dressings. In one aspect, a two-piece dressing includes a drape including a first light switchable adhesive, and a pad. The pad includes a second light switchable adhesive configured to couple the pad to the drape and a light source configured to emit light and activate at least the second light switchable adhesive. In another aspect a two-piece dressing includes a drape and a pad. The pad is configured to be coupled to the drape and to a light source, and the pad includes a light switchable adhesive configured to couple the pad to the drape. The light source is configured to emit light to activate the light switchable adhesive to decouple the pad from the drape, and the pad is configured to direct the light to activate second light switchable adhesive to decouple the drape from a tissue site.

21 Claims, 11 Drawing Sheets

(51) Int. Cl.
*A61F 13/05* (2024.01)
*A61L 24/00* (2006.01)
*A61L 24/04* (2006.01)

(52) U.S. Cl.
CPC .......... *A61L 24/001* (2013.01); *A61L 24/043* (2013.01); *A61M 2209/06* (2013.01)

(58) Field of Classification Search
CPC . A61F 2013/00757; A61F 2013/53925; Y10T 428/28; A61L 15/58; A61L 15/585; A61L 24/00; A61L 24/001; A61L 24/043; A61M 1/91; A61M 1/912
See application file for complete search history.

(56) References Cited

U.S. PATENT DOCUMENTS 2,632,443 A 3/1953 Lesher
2,682,873 A 7/1954 Evans et al.
2,910,763 A 11/1959 Lauterbach
2,969,057 A 1/1961 Simmons
3,066,672 A 12/1962 Crosby, Jr. et al.
3,367,332 A 2/1968 Groves
3,520,300 A 7/1970 Flower, Jr.
3,568,675 A 3/1971 Harvey
3,648,692 A 3/1972 Wheeler
3,682,180 A 8/1972 McFarlane
3,826,254 A 7/1974 Mellor
4,080,970 A 3/1978 Miller
4,096,853 A 6/1978 Weigand
4,139,004 A 2/1979 Gonzalez, Jr.
4,165,748 A 8/1979 Johnson
4,184,510 A 1/1980 Murry et al.
4,233,969 A 11/1980 Lock et al.
4,245,630 A 1/1981 Lloyd et al.
4,256,109 A 3/1981 Nichols
4,261,363 A 4/1981 Russo
4,275,721 A 6/1981 Olson
4,284,079 A 8/1981 Adair
4,297,995 A 11/1981 Golub
4,333,468 A 6/1982 Geist
4,373,519 A 2/1983 Errede et al.
4,382,441 A 5/1983 Svedman
4,392,853 A 7/1983 Muto
4,392,858 A 7/1983 George et al.
4,419,097 A 12/1983 Rowland
4,465,485 A 8/1984 Kashmer et al.
4,475,909 A 10/1984 Eisenberg
4,480,638 A 11/1984 Schmid
4,525,166 A 6/1985 Leclerc
4,525,374 A 6/1985 Vaillancourt
4,540,412 A 9/1985 Van Overloop
4,543,100 A 9/1985 Brodsky
4,548,202 A 10/1985 Duncan
4,551,139 A 11/1985 Plaas et al.
4,569,348 A 2/1986 Hasslinger
4,605,399 A 8/1986 Weston et al.
4,608,041 A 8/1986 Nielsen
4,640,688 A 2/1987 Hauser
4,655,754 A 4/1987 Richmond et al.
4,664,662 A 5/1987 Webster
4,710,165 A 12/1987 McNeil et al.
4,733,659 A 3/1988 Edenbaum et al.
4,743,232 A 5/1988 Kruger
4,758,220 A 7/1988 Sundblom et al.
4,787,888 A 11/1988 Fox
4,826,494 A 5/1989 Richmond et al.
4,838,883 A 6/1989 Matsuura
4,840,187 A 6/1989 Brazier
4,863,449 A 9/1989 Therriault et al.
4,872,450 A 10/1989 Austad
4,878,901 A 11/1989 Sachse
4,897,081 A 1/1990 Poirier et al.
4,906,233 A 3/1990 Moriuchi et al.
4,906,240 A 3/1990 Reed et al.
4,919,654 A 4/1990 Kalt
4,941,882 A 7/1990 Ward et al.
4,953,565 A 9/1990 Tachibana et al.
4,969,880 A 11/1990 Zamierowski
4,985,019 A 1/1991 Michelson
5,037,397 A 8/1991 Kalt et al.
5,086,170 A 2/1992 Luheshi et al.
5,092,858 A 3/1992 Benson et al.
5,100,396 A 3/1992 Zamierowski
5,134,994 A 8/1992 Say
5,149,331 A 9/1992 Ferdman et al.
5,167,613 A 12/1992 Karami et al.
5,176,663 A 1/1993 Svedman et al.
5,215,522 A 6/1993 Page et al.
5,232,453 A 8/1993 Plass et al.
5,261,893 A 11/1993 Zamierowski
5,278,100 A 1/1994 Doan et al.
5,279,550 A 1/1994 Habib et al.
5,298,015 A 3/1994 Komatsuzaki et al.
5,342,376 A 8/1994 Ruff
5,344,415 A 9/1994 DeBusk et al.
5,358,494 A 10/1994 Svedman
5,437,622 A 8/1995 Carion
5,437,651 A 8/1995 Todd et al.
5,527,293 A 6/1996 Zamierowski
5,549,584 A 8/1996 Gross
5,556,375 A 9/1996 Ewall
5,607,388 A 3/1997 Ewall
5,636,643 A 6/1997 Argenta et al.
5,645,081 A 7/1997 Argenta et al.
6,071,267 A 6/2000 Zamierowski
6,135,116 A 10/2000 Vogel et al.
6,241,747 B1 6/2001 Ruff
6,287,316 B1 9/2001 Agarwal et al.
6,345,623 B1 2/2002 Heaton et al.
6,488,643 B1 12/2002 Tumey et al.
6,493,568 B1 12/2002 Bell et al.
6,553,998 B2 4/2003 Heaton et al.
6,814,079 B2 11/2004 Heaton et al.
7,846,141 B2 12/2010 Weston
8,062,273 B2 11/2011 Weston
8,216,198 B2 7/2012 Heagle et al.
8,251,979 B2 8/2012 Malhi
8,257,327 B2 9/2012 Blott et al.
8,398,614 B2 3/2013 Blott et al.
8,449,509 B2 5/2013 Weston
8,529,548 B2 9/2013 Blott et al.
8,535,296 B2 9/2013 Blott et al.
8,551,060 B2 10/2013 Schuessler et al.
8,568,386 B2 10/2013 Malhi
8,679,081 B2 3/2014 Heagle et al.
8,834,451 B2 9/2014 Blott et al.
8,926,592 B2 1/2015 Blott et al.
9,017,302 B2 4/2015 Vitaris et al.
9,040,076 B2 * 5/2015 Tunius .................. C09J 183/04
424/445
9,198,801 B2 12/2015 Weston
9,211,365 B2 12/2015 Weston
9,289,542 B2 3/2016 Blott et al.
2002/0077661 A1 6/2002 Saadat
2002/0115951 A1 8/2002 Norstrem et al.
2002/0120185 A1 8/2002 Johnson
2002/0143286 A1 10/2002 Tumey
2014/0163491 A1 6/2014 Schuessler et al.
2015/0080788 A1 3/2015 Blott et al.
2018/0021178 A1 * 1/2018 Locke ................ A61F 13/0206
602/43
2019/0192751 A1 6/2019 Locke et al.
2020/0337908 A1 * 10/2020 Long ...................... A61F 13/05
2020/0385614 A1 * 12/2020 Locke .................. A61L 15/585

FOREIGN PATENT DOCUMENTS

AU 755496 B2 12/2002
CA 2005436 A1 6/1990
DE 26 40 413 A1 3/1978
DE 43 06 478 A1 9/1994
DE 29 504 378 U1 9/1995
DE 202017000986 U1 3/2017

(56) References Cited

FOREIGN PATENT DOCUMENTS

| | | | |
|---|---|---|---|
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |

OTHER PUBLICATIONS

International Search Report and Written Opinion for Corresponding Application No. PCT/IB2020/059724, mailed Feb. 16, 2021.

Louis C. Argenta, Md and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, . Maksimovi?, ?. Radak, and P. Peška, "Vacuum Therapy in the Treatment of Peripheral Blood Vessels," Timok Medical Journal 11 (1986), pp. 161-164 (certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

(56) References Cited

OTHER PUBLICATIONS

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

TWO-PIECE DRESSING INCLUDING SWITCHABLE ADHESIVE

CROSS-REFERENCE TO RELATED APPLICATIONS

This application claims the benefit of priority to U.S. Provisional Application No. 62/924,950, filed on Oct. 23, 2019, which is incorporated herein by reference in its entirety.

TECHNICAL FIELD

Aspects of the present disclosure relate generally to a wound therapy system, and more specifically, but not by way of limitation, to a negative pressure wound therapy device including a light switchable adhesive and an apparatus, system, and method for using the therapy device.

BACKGROUND

Light switchable (switched or light switched) adhesives are pressure sensitive adhesives that are "switchable" from a tacky state to a non-tacky or low-tack state in which the switched adhesive has a reduced peel strength relative to the peel strength of the adhesive before switching Light switchable adhesives have been included in therapy systems such as wound dressings and bandages for use in negative-pressure wound therapy ("NPWT"). To illustrate, the high peel strength of light switchable adhesives in the tacky state enables a strong seal during NPWT, and the low peel strength of the light switchable adhesives in the non-tacky or low-tack state enable easy pain free removal. While the two states of light switchable adhesives enable a better patient experience, additional components, as compared to non-switchable adhesive and conventional adhesive, may be utilized to switch the light switchable adhesives between states.

For example, some conventional systems, such as systems that utilize infrared or ultraviolet light, that employ light switchable adhesives may require a separate device to activate (i.e., switch between tacky and non-tacky states) the light switchable adhesive. To illustrate, a separate light source may be used to activate the light switchable adhesive. Thus, the patient either has to carry a separate device, wait for a care provider, or visit provider facility (e.g., hospital) each time a dressing including light switchable adhesive is set to be changed or removed. Additionally, the separate devices may be lost or damaged by a patient.

As another example, other conventional systems that utilize visible light may utilize one or more light blocking layers to protect or reduce exposure of the light switchable adhesive to ambient light. The light blocking layers may increase the time of removal of the light switchable adhesive. To illustrate, a technician may require extra time to direct UV light past the light blocking layers to reach each side of the drape to activate the light switchable adhesive Thus, conventional systems that employ light switchable adhesives utilize additional components and steps, which may increase cost and decrease ease of use, as compared to non-light switchable adhesive dressings.

Therefore, while conventional light switchable adhesive dressings offer improved patient comfort, such dressing utilize additional components and/or steps, as compared to non-light switchable adhesive dressings.

SUMMARY

The present disclosure describes devices, systems, and methods related to a light switchable adhesive therapy system. The light switchable adhesive therapy system may include a wound dressing that includes a light switchable adhesive. The wound dressing may include a two-piece removable dressing for facilitating removal of the wound dressing from a tissue site by allowing easier access to activate the light switchable adhesive attached to the tissue site. For example, the wound dressings described herein include a pad and a drape, each including a separate light switchable adhesive, where the pad and the drape may be decoupled from each other to allow greater access to the drape for removing or changing the wound dressing or a portion thereof. To illustrate, once the pad is decoupled from the drape, the pad may be used to direct a light to the light switchable adhesive that couples the drape to a tissue site of a patient. Accordingly, by using the wound dressing to direct the light, the wound dressing may have a reduced amount of layers, be easier to wear, and be easier to remove, as compared to wound dressings which are switched by remote light sources and/or are switched while the pad is attached to the drape.

In some implementations, either the drape, the pad, or both are re-used and absorbent material (e.g., manifold) is replaced. To illustrate, the pad may cover an opening defined by the drape where the absorbent material is placed, and once the pad is decoupled from the drape the absorbent material may be replaced without the removal of the drape. Alternatively, after the pad is decoupled form the drape, the pad may be used to remove the drape, by directing a light to activate the light switchable adhesive of the drape, and then coupled to a new drape. In this way, the wound dressing can minimize the cost of replacing the wound dressing by allowing replacement of only a single component when needed.

Furthermore, a light source for activating the light switchable adhesive of the wound dressing may be incorporated into existing components of the therapy system (e.g., a negative-pressure wound therapy system) to transition (e.g., deactivate) the light switchable adhesive of the wound dressing (e.g., a separable or multi-piece wound dressing). In some implementations, the light source may be incorporated within a tube that connects the wound dressing to a negative-pressure source or other therapy device during treatment. Alternatively, some implementations may include a light source that is coupled to the pad of the wound dressing to enable removal of the dressing without additional components, such as external light sources, light pipes, etc. Accordingly, by integrating the light source with the pad or other existing equipment, the wound dressing can decouple the pad and drape automatically without the need for an external light source. In this way, cost of treatment may be reduced by eliminating the risk of a patient losing or damaging the external light source Additionally, a wound dressing (e.g., a smart wound dressing) may include one or more electronics coupled to the pad to activate the light source or communicate with another device. In this way, improved or additional monitoring of the tissue site may be available without the assistance of a care provider, or a visit to a care provider facility. Likewise, the smart wound dressing may provide automated control to enable a care provider to expedite or delay replacement of the wound dressing remotely, based on information recorded by the wound dressing. For example, the smart wound dressing may monitor a temperature and notify the doctor of any abnormal temperature increase at the tissue site that may indicate an infection of the wound. Accordingly, the present disclosure provides a multi-piece wound dressing and light source having a minimal number of outside devices required to remove the light switchable wound dressing, thereby avoiding extra cost, added removal time, or extra visits to a health care provider.

Some embodiments of the present wound dressings comprise: a drape including a first light switchable adhesive; and a pad including: a second light switchable adhesive configured to couple the pad to the drape, and a light source configured to emit light and activate at least the second light switchable adhesive.

In some of the foregoing embodiments of the present wound dressings, the wound dressings further comprise a power source coupled to the drape or the pad. Additionally or alternatively, the power source is configured to be coupled to the light source to enable delivery of the light to the first light switchable adhesive and the second light switchable adhesive.

In some of the foregoing embodiments of the present wound dressings, the wound dressings further comprise one or more electronic communication devices disposed on the drape or the pad. In some implementations, the one or more electronic communication devices comprise an antenna, an inductor, a printed circuit board (PCB), a near-field communication (NFC) circuit, or a Bluetooth low energy (BLE) circuit. Additionally or alternatively, the one or more electronic communication devices are configured to wirelessly communicate with a remote device or a therapy device to enable activation of the light source.

In some of the foregoing embodiments of the present wound dressings, the first and the second light switchable adhesives comprise: one or more polymers; and photo initiators configured to cause the one or more polymers to cross-link responsive to receiving the light. In some such implementations, the photo initiators have a peak absorbance between 200 nanometers (nm) to 400 nm or between 750 nm to 860 nm.

In some of the foregoing embodiments of the present wound dressings, the wound dressings further comprise a shroud coupled to an exterior surface of the drape of the dressing, the shroud configured to reflect the light within the dressing, block second light from entering the dressing, or both.

Some other embodiments of the present wound dressings comprise: a drape including a first light switchable adhesive configured to couple the drape to a tissue site; and a pad configured to be coupled to the drape and to a light source, the pad including: a second light switchable adhesive configured to couple the pad to the drape, wherein: the light source is configured to emit light to activate at least the second light switchable adhesive to decouple the pad from the drape; and while the pad is coupled to the light source and decoupled from the drape, the pad is configured to direct the light and is moveable relative to the drape to activate the first light switchable adhesive to decouple the drape from the tissue site.

In some of the foregoing embodiments of the present wound dressings, the wound dressings further comprise a tube coupled to the pad, the tube configured to deliver light from the light source. In some implementations, the light source is included in or on a connector of the tube.

In some of the foregoing embodiments of the present wound dressings, the wound dressings further comprise a therapy device coupled to the tube and configured to active the light source, the therapy device including the light source. Additionally or alternatively, the wound dressings further comprise a cover film removeably coupled to the first light switchable adhesive.

In some of the foregoing embodiments of the present wound dressings, the first and second light switchable adhesive includes photo initiators configured to absorb or react with UV light, visible light, or both. Additionally or alternatively, the first or second light switchable adhesives comprise a dual light switchable adhesive.

Some embodiments of the present therapy systems comprise: a wound dressing of any of the foregoing embodiments; a therapy device configured to couple to the wound dressing and configured to activate the light source; wherein the light source is configured to activate the first light switchable adhesive and second light switchable adhesive. In some implementations, the wound dressings further comprise an absorbent material.

In some of the foregoing embodiments of the present therapy systems, the present therapy systems further comprise tubing configured to couple the therapy device to the wound dressing. Additionally or alternatively, the present therapy systems further comprise a remote device in communication with the therapy device or the light source, the remote device configured to cause the therapy device to active the light source of the wound dressing.

In some of the foregoing embodiments of the present therapy systems, the therapy device is configured to apply positive-pressure, reduced-pressure, or both to the dressing. Additionally or alternatively, the therapy device comprises a controller configured to control operation of the therapy device, the light source, or both.

Some embodiments of the present therapy systems comprise: a wound dressing any of the foregoing embodiments; a therapy device configured to couple to the wound dressing, wherein the light source is configured to activated by a remote device distinct from the therapy device. In some implementations, the wound dressing further comprises an absorbent material. Additionally, or alternatively, the remote device is a smart phone.

Some embodiments of the present methods comprise: receiving, by a pad of a wound dressing, a light activation signal; and activating, by the pad, a light source of the wound dressing to emit light responsive to the light activation signal, the light configured to active a light switchable adhesive of the wound dressing.

In some of the foregoing embodiments of the present methods, the present methods further comprise directing, by the pad, the light source to the light switchable adhesive, the light switchable adhesive configured to couple the pad to a drape of the wound dressing. Additionally, or alternatively, the present methods further comprise, responsive to being moved, directing, by the pad, the light source to a second light switchable adhesive, the second light switchable adhesive configured to couple the pad to a drape of the wound dressing. In some of the foregoing embodiments of the present methods, the present methods further comprise receiving the light activation signal at a controller of the pad prior to activating the light source by the controller.

Some embodiments of the present methods (e.g., methods of operating a therapy system) comprise: receiving, at a therapy device, an activation input; and transmitting, by the therapy device, a light activation signal to a wound dressing based on the activation input, the light activation signal configured to cause a light source of the wound dressing to emit a light responsive to the light activation signal.

In some of the foregoing embodiments of the present methods, receiving the activation input comprises receiving the activation input from a remote device. Additionally, or alternatively, the activation input is generated at the therapy device based on a timer, or a user input. In some of the foregoing embodiments of the present methods, the present methods further comprise setting a timer associated with the light activation signal, wherein the light source emits the light responsive to expiration of the timer.

Some embodiments of the present methods (e.g., methods of using a wound dressing) comprise: activating a light source coupled to a wound dressing, the wound dressing comprising a pad and a drape, wherein activating the light source causes light from the light source to activate a first light switchable adhesive to decouple the pad from the drape; detaching the pad from the drape; directing the light to a second light switchable adhesive of the drape to decouple the drape from a tissue site; and detaching the drape from the tissue site.

In some of the foregoing embodiments of the present methods, directing the light to the second light switchable adhesive comprises moving the pad to direct the light to activate the second light switchable adhesive of the drape. Additionally, or alternatively, moving the pad to direct the light further comprises moving the pad relative to the drape while the drape is coupled to a patient. In some implementations, activating the light source comprises providing an input to a remote device.

In some of the foregoing embodiments of the present methods, the present methods further comprise attaching the wound dressing to a tissue site of a patient. In some implementations, attaching the wound dressing further comprises: attaching the drape to the tissue site of the patient via the second light switchable adhesive; removing a portion of the drape; and attaching the pad to the drape via the first light switchable adhesive such that the pad covers the portion of the drape.

In some of the foregoing embodiments of the present methods, the present methods further comprise, prior to attaching, removing a cover film from the pad, the drape, or both. Additionally, or alternatively, the present methods further comprise connecting a tube to the wound dressing, the tube configured to communicate the light from the light source to the pad.

In some of the foregoing embodiments of the present methods, the present methods further comprise connecting a therapy device to the wound dressing, wherein the therapy device activates the light source, wherein the light source is included in the therapy device or the tube. Additionally, or alternatively, activating a light source further comprises directing the light to a first light switchable adhesive to decouple the pad from the drape, from an absorbent material, or both, of the wound dressing.

Some embodiments of the present kits (e.g., a kit for a wound dressing) comprise: a wound dressing including: a drape including a first light switchable adhesive; a pad including a second light switchable adhesive; and a light source configured to be coupled to the pad. In some embodiments of the present kits, the present kits further comprises a package that includes the wound dressing.

As used herein, the term "switchable" will be used to refer to adhesives which can be changed from a high tack and/or peel strength state/phase to a low tack and/or peel strength state/phase (e.g., non-tacky state). Recognizing that the expression "low tack and/or peel strength" is a relative term, it will be defined here as meaning a condition of a minimum reduction in tackiness which the adhesive reaches after switching from the high tack and/or peel strength state/phase. The reduction in tack or peel force may be as great as 99% or as little as 30%. Typically, the reduction in tack or peel force is between 70%. and 90%.

As used herein, various terminology is for the purpose of describing particular implementations only and is not intended to be limiting of implementations. For example, as used herein, an ordinal term (e.g., "first," "second," "third," etc.) used to modify an element, such as a structure, a component, an operation, etc., does not by itself indicate any priority or order of the element with respect to another element, but rather merely distinguishes the element from another element having a same name (but for use of the ordinal term). The term "coupled" is defined as connected, although not necessarily directly, and not necessarily mechanically. Additionally, two items that are "coupled" may be unitary with each other. To illustrate, components may be coupled by virtue of physical proximity, being integral to a single structure, or being formed from the same piece of material. Coupling may also include mechanical, thermal, electrical, communicational (e.g., wired or wireless), or chemical coupling (such as a chemical bond) in some contexts.

The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. As used herein, the term "approximately" may be substituted with "within 10 percent of" what is specified. Additionally, the term "substantially" may be substituted with "within [a percentage] of" what is specified, where the percentage includes 0.1, 1, or 5 percent; or may be understood to mean with a design, manufacture, or measurement tolerance. The phrase "and/or" means and or. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including"). As a result, an apparatus that "comprises," "has," or "includes" one or more elements possesses those one or more elements, but is not limited to possessing only those one or more elements. Likewise, a method that "comprises," "has," or "includes" one or more steps possesses those one or more steps, but is not limited to possessing only those one or more steps.

Any aspect of any of the systems, methods, and article of manufacture can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb. Additionally, it will be understood that the term "wherein" may be used interchangeably with "where."

Further, a device or system that is configured in a certain way is configured in at least that way, but it can also be configured in other ways than those specifically described. The feature or features of one embodiment may be applied to other embodiments, even though not described or illustrated, unless expressly prohibited by this disclosure or the nature of the embodiments.

Some details associated with the aspects of the present disclosure are described above, and others are described below. Other implementations, advantages, and features of the present disclosure will become apparent after review of the entire application, including the following sections: Brief Description of the Drawings, Detailed Description, and the Claims.

BRIEF DESCRIPTION OF THE DRAWINGS

A further understanding of the nature and advantages of the present disclosure may be realized by reference to the following drawings. The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Figure 1:
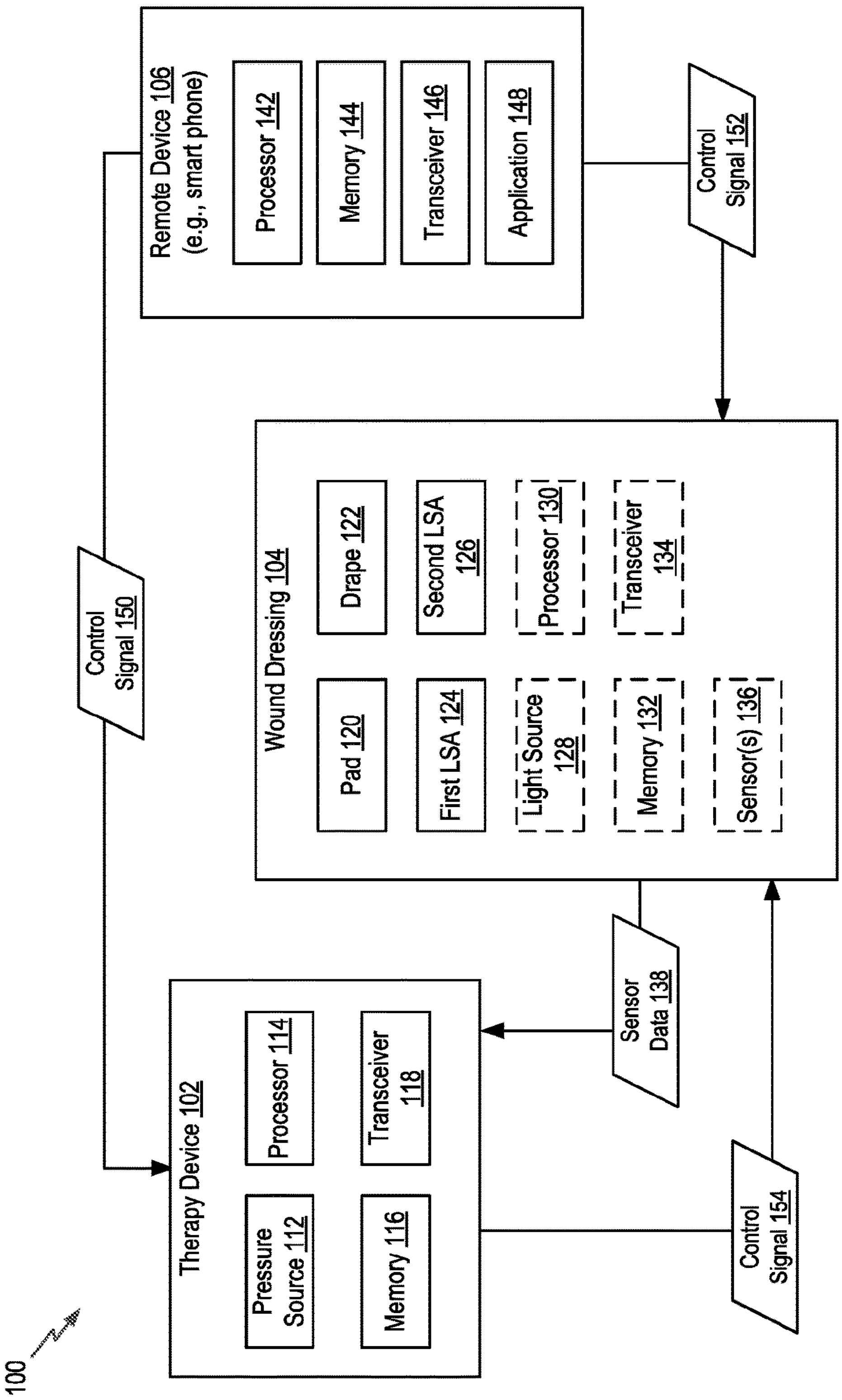
FIG. 1 is a block diagram of an example of a light switchable adhesive therapy system.

As used herein, the terms "tissue site" and "target tissue" as used herein can broadly refer to a wound (e.g., open or closed), a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The terms "tissue site" and "target tissue" as used herein can also refer to a surrounding tissue area(s) and/or areas of tissue that are not necessarily wounded or exhibit a disorder, but include tissue that would benefit from tissue generation and/or tissue that may be harvested and transplanted to another tissue location. The terms "tissue site" and "target tissue" may also include incisions, such as a surgical incision. In some implementations, "target tissue" may correspond or refer to a wound, and "tissue site" may correspond or refer to a tissue area(s) surrounding and including the target tissue. Additionally, the term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft. A wound may include chronic, acute, traumatic, subacute, and dehisced wounds, partial-thickness burns, ulcers (such as diabetic, pressure, or venous insufficiency ulcers), flaps, grafts, and fistulas, for example.

The term "positive-pressure" (or "hyperbaric") as used herein generally refers to a pressure greater than a local ambient pressure, such as the ambient pressure in a local environment external to a sealed therapeutic environment (e.g., an internal volume). In most cases, this positive-pressure will be greater than the atmospheric pressure at which the patient is located. Alternatively, the positive-pressure may be greater than a hydrostatic pressure associated with tissue at the tissue site. Unless otherwise indicated, values of pressure stated herein are gauge pressures. References to increases in positive-pressure typically refer to an increase in absolute pressure, and decreases in positive-pressure typically refer to a decrease in absolute pressure. Additionally, the process of increasing pressure may be described illustratively herein as "applying", "delivering," "distributing," "generating", or "providing" positive-pressure, for example.

The term "reduced-pressure" (and "negative-pressure" or "hypobaric") as used herein generally refers to a pressure less than a local ambient pressure, such as the ambient pressure in a local environment external to a sealed therapeutic environment (e.g., an internal volume). In most cases, this reduced-pressure will be less than the atmospheric pressure at which the patient is located. Alternatively, the reduced-pressure may be less than a hydrostatic pressure associated with tissue at the tissue site. Unless otherwise indicated, values of pressure stated herein are gauge pressures. References to increases in reduced-pressure typically refer to a decrease in absolute pressure, and decreases in reduced-pressure typically refer to an increase in absolute pressure. Additionally, the process of reducing pressure may be described illustratively herein as "applying", "delivering," "distributing," "generating", or "providing" reduced-pressure, for example.

The term "fluid" may refer to liquid, gas, air, or a combination thereof. The term "fluid seal," or "seal," means a seal adequate to maintain a pressure differential (e.g., positive-pressure or reduced-pressure) at a desired site given the particular pressure source or subsystem involved. Similarly, it may be convenient to describe certain features in terms of fluid "inlet" or "outlet" in such a frame of reference. However, the fluid path may also be reversed in some applications, such as by substituting a reduced-pressure source (negative or hypobaric pressure source) for a positive-pressure source, and this descriptive convention should not be construed as a limiting convention.

FIG. 1 shows a block diagram of an illustrative system 100 (e.g., a light switchable adhesive therapy system) for wound therapy. System 100 may include a therapy device 102, a wound dressing 104, and a remote device 106. System 100 is configured to provide a treatment to a tissue site associated with a target area of a patient. For example, system 100 may be configured for use in negative-pressure wound therapy ("NPWT"). Specifically, one or more components (e.g., 102-106) of system 100 may be in fluid communication with tissue site to create a vacuum around the tissue site, and/or to remove fluid from or provide fluid to the tissue site. To illustrate, dressing 104 may be in fluid communication with tissue site and may be in fluid communication with therapy device 102. In some implementations, system 100 may include one or more components commercially available through and/or from KCI USA, Inc. of San Antonio, Tex., U.S.A., and/or its subsidiary and related companies (collectively, "KCI").

Therapy device 102 is configured to provide a treatment to tissue site. As illustrated in the block diagram of FIG. 1, therapy device 102 includes or is associated with a pressure source 112. In some implementations, pressure source 112 is a negative-pressure treatment apparatus configured to generate and provide negative pressure to a tissue site (e.g., 208). Providing negative pressure to tissue site enables sealing of a target tissue with dressing 104, increases adhesion of dressing 104 (e.g., a light switchable adhesive) to tissue site, enables fluid removal from tissue site (e.g., exudate from target tissue), or a combination thereof.

In some implementations, therapy device 102 includes pressure source 112, such as a vacuum source (e.g., a pump and/or the like), configured to be actuatable (and/or actuated) to apply reduced-pressure (e.g., negative pressure) to dressing 104. In such implementations, therapy device 102 may alternate between providing positive-pressure therapy and negative-pressure therapy to the dressing 104, may provide positive-pressure therapy to a first portion of the dressing 104 and negative-pressure therapy to a second portion of dressing 104, may provide no positive or negative pressure, or a combination thereof. In some such implementations, therapy device 102 can provide positive-pressure therapy and negative-pressure therapy to the dressing 104 at the same time (e.g., partially concurrently). As illustrative, non-limiting examples, reduced-pressure applied to a tissue site may typically ranges between −5 millimeters mercury (mm Hg) (−667 pascals (Pa)) and −500 mm Hg (−66.7 kilo (k) Pa). Common therapeutic ranges are between −75 mm Hg (−9.9 kPa) and −300 mm Hg (−39.9 kPa).

As an illustrative, non-limiting example, pressure source 112 may be a positive-pressure treatment apparatus configured to provide a fluid (e.g., liquid, gas, or mixture) to tissue site 108. Specifically, pressure source 112 may provide oxygen to dressing 104 surrounding tissue site 108 at a positive-pressure. In some implementations, pressure source 112 may comprise, for example, a pressurized oxygen container, an oxygen concentrator, or an oxygen collector (e.g., a pump and a filter) and/or the like, configured to be actuatable (and/or actuated) to apply positive-pressure (e.g., hyperbaric pressure) to dressing 104. As another example, pressure source 112 may include a medication delivery device configured to deliver medication to tissue site 108. In some implementations, pressure source 112 may be able to simultaneously, or alternately, provide a positive pressure and negative pressure to dressing 104 or tissue site 108.

As shown in FIG. 1, therapy device 102 may include a processor 114, a memory 116 (e.g., a computer-readable storage device), and a transceiver 118 (e.g., transmitter and/or receiver). Processor 114 may be electronically, or physically, coupled to memory 116 and transceiver 118. Processor 114 may include a microcontroller/microprocessor, a central processing unit (CPU), a field-programmable gate array (FPGA) device, an application-specific integrated circuits (ASIC), another hardware device, a firmware device, or any combination thereof. Processor 114 may be configured to execute instructions, execute and/or operate according to specified parameters, and process data from one or more sensors (e.g., 136).

Memory 116, such as a non-transitory computer-readable storage medium, may include volatile memory devices (e.g., random access memory (RAM) devices), nonvolatile memory devices (e.g., read-only memory (ROM) devices, programmable read-only memory, and flash memory), or both. Memory 116 may be configured to store instructions (e.g., commands that, when executed by processor 114, cause the processor to perform one or more operations), thresholds, or other parameters.

Transceiver 118 is configured to communicate (e.g., transmit and receive data) with other components of system 100, such as wound dressing 104 and/or remote device 106. In some implementations, transceiver 118 may transmit and receive instructions, data, or other operations between processor 114 and memory 116, or between therapy device 102 and other external devices (e.g., dressing 104, remote device 106, and/or the like).

Therapy device 102 may also include one or more other components, such as a sensor, an alarm indicator, a database, software, a display device, a user interface, a regulator, and/or another component, that further facilitate wound therapy.

Wound dressing 104 is configured to be positioned on, or coupled to, the patient during wound therapy, such as a tissue site thereof. Wound dressing 104 includes a pad 120 (also referred to as a connector or a dressing connection pad) and a drape 122. Details of pad 120 and drape 122 are described further with reference to FIG. 3. Wound dressing 104 includes at least one light switchable adhesive (LSA), such as first LSA 124, and optionally includes an additional LSA, such as second LSA 126.

Pad 120 may be configured to couple wound dressing 104 to external therapeutic devices (e.g., therapy device 102, remote device 106, etc.). Pad 120 may be selectively coupled to drape 122. To illustrate, pad 120 may be coupled to drape 122 via a second LSA 126. In some implementations, pad 120 is directly coupled to drape 122 via second LSA 126, while in other implementations, one or more intervening layer are positioned between pad 120 and drape 122; in yet other implementations, a separate adhesive drape disposed over at least a portion of pad 120 and at least a portion of drape 122, as illustrative, non-limiting examples.

Drape 122 may be configured to couple dressing 104 at tissue site 108 and/or to provide a seal to create an enclosed space (e.g., an interior volume) corresponding to tissue site 108. For example, drape 122 may be configured to provide a fluid seal between two components and/or two environments, such as between a sealed therapeutic environment and a local ambient environment. To illustrate, when coupled to tissue site 108, drape 122 is configured to maintain a pressure differential at tissue site 108. In some implementations, pressure differential may be provided by therapy device 102, pad 120, or another pressure source. Additionally, drape 122 may seal or block ambient light from transmission to tissue site 108 and/or adhesives attached thereto. Drape 122 may include a drape aperture that extends through drape 122 to enable fluid communication between therapy device 102, pad 120, and tissue site 108.

Drape 122 may be coupled to a tissue site via one or more LSAs, such as a medically acceptable, pressure-sensitive adhesive that extends about a periphery, a portion, or an entirety of drape 122. To illustrate, drape 122 may be coupled to the pad 120 via a first LSA 124 and may be coupled to a tissue site via a second LSA 126. Additionally, or alternatively, drape 122 may be coupled to a tissue site via a double-sided drape tape, paste, hydrocolloid, hydrogel, and/or other sealing device or element, as illustrative, non-limiting examples. In some implementations, drape 122 includes a cavity or conduit to transport and/or diffuse received light to adhesives (e.g., adhesive 124) attached to drape 122 and/or tissue site 108, as described further with reference to FIG. 3.

First and second LSAs 124, 126 may include one or more one or more polymers; and one or more photo initiators configured to cause the one or more polymers to cross-link responsive to receiving a light. For example, the LSAs described herein include photo initiators that are receptive to high wavelength UV light, such as UVC UV light. Such light switchable adhesives may not need covers or sheaths as ambient light does not typically include UVC light. For example, UVC light is not produced by commercial/conventional lighting devices used for illumination and UVC from the Sun is absorbed by the atmosphere. In other implementations, the first and second LSAs 124, 126 include photo initiators configured to absorb or react with UV light, visible light, or both. In some implementations, the photo initiators have a peak absorbance between 200 nanometers (nm) to 400 nm or between 750 nm to 860 nm. First and second LSAs 124, 126 may be configured for single use (e.g., single light switchable adhesive) or multi-use (e.g., dual light switchable adhesive).

First and second LSAs 124, 126 may additionally or alternatively include polymerization initiators configured to cause the one or more polymers to cross-link responsive to receiving a stimulus, such as energy or moisture. Such switchable adhesives may include dual switchable adhesives (e.g., when both types of initiators are used) when multiple types of stimuli are used to switch the adhesives. First and second LSA 124, 126 may be the same or different. For example, a higher peel strength LSA may be used to keep the pad 120 and drape 122 together to prevent separation, or may be used to bond to the tissue site such that the pad 120 decouples from the drape 122 more easily. As another example, different thickness or patterns may be used for the LSAs. To illustrate, a thicker application of LSA which bonds to the patient may provide a more robust seal and enable a single drape 122 to be used with multiple pads 120. As yet another example, the LSAs may respond or switch based on different types of light, such as different type of light of the same spectrums or lights from different spectrums.

In some implementations, system 100 includes a light source 128 configured to emit light. Light source 128 may be operable at a particular spectrum or wavelength to activate (i.e., transition between a high-tack state and a low-tack state) a LSA (e.g., 124, 126). Transitioning from the high-tack state to the low-tack state enables easy, pain and trauma free removal of dressing 104 and/or easy disconnection of components coupled via a LSA. As illustrated in FIG. 1, dressing 104 includes or is associated with light source 128. In some implementations, light source 128 may be coupled to drape 122, pad 120, or both. For example, light source 128 may be positioned on dressing 104 such that when light source 128 is activated and a light is emitted, the light is configured to activate second light switchable adhesive 126 to decouple pad 120 from drape 122. In other implementations, light source 128 may be positioned at a location upstream from dressing 104. To illustrate, light source may be positioned within a tube (e.g., FIG. 6) or therapy device 102 (e.g., FIGS. 4A, 5A, and 6).

Light source 128 may be used to decouple all, or part of, dressing 104 from a patient. For example, wound dressing 104 may include a two-piece (e.g., pad 120 and drape 122) removable dressing for facilitating removal of the wound dressing from a tissue site by allowing easier access to activate the light switchable adhesive. To illustrate, drape 122 includes first LSA 124 that is separate from second LSA that is included on pad 120. This allows for pad 120 and drape 122 to be decoupled from each other to allow greater access to the drape for removing or changing the wound dressing or a portion thereof. In some implementations, light source 128 may include any suitable component configured to generate light or electromagnetic radiation having a wavelength of 10-400 nanometers (e.g., one or more LEDs, incandescent light source, fluorescent light source, halogen light source, or the like). In other implementations, light source 128 may include or correspond to a UV Laser, such as a gas laser, a laser diode, a solid-state laser, an excimer laser, or a combination thereof. In some implementations, UV laser is configured to generate coherent light (e.g., a laser beam) having electromagnetic radiation of UV wavelengths. For example, UV laser is a UVA laser (315-400 nm), a UVB laser (280-315 nm), a UVC laser (100-280 nm), or an extreme UV laser (10-121 nm). In other implementations, visible and/or infrared (IR) light may be used. For example, light source 128 may generate and emit IR light and one or more of the LSAs may switch responsive to the IR light.

Figure 2A:
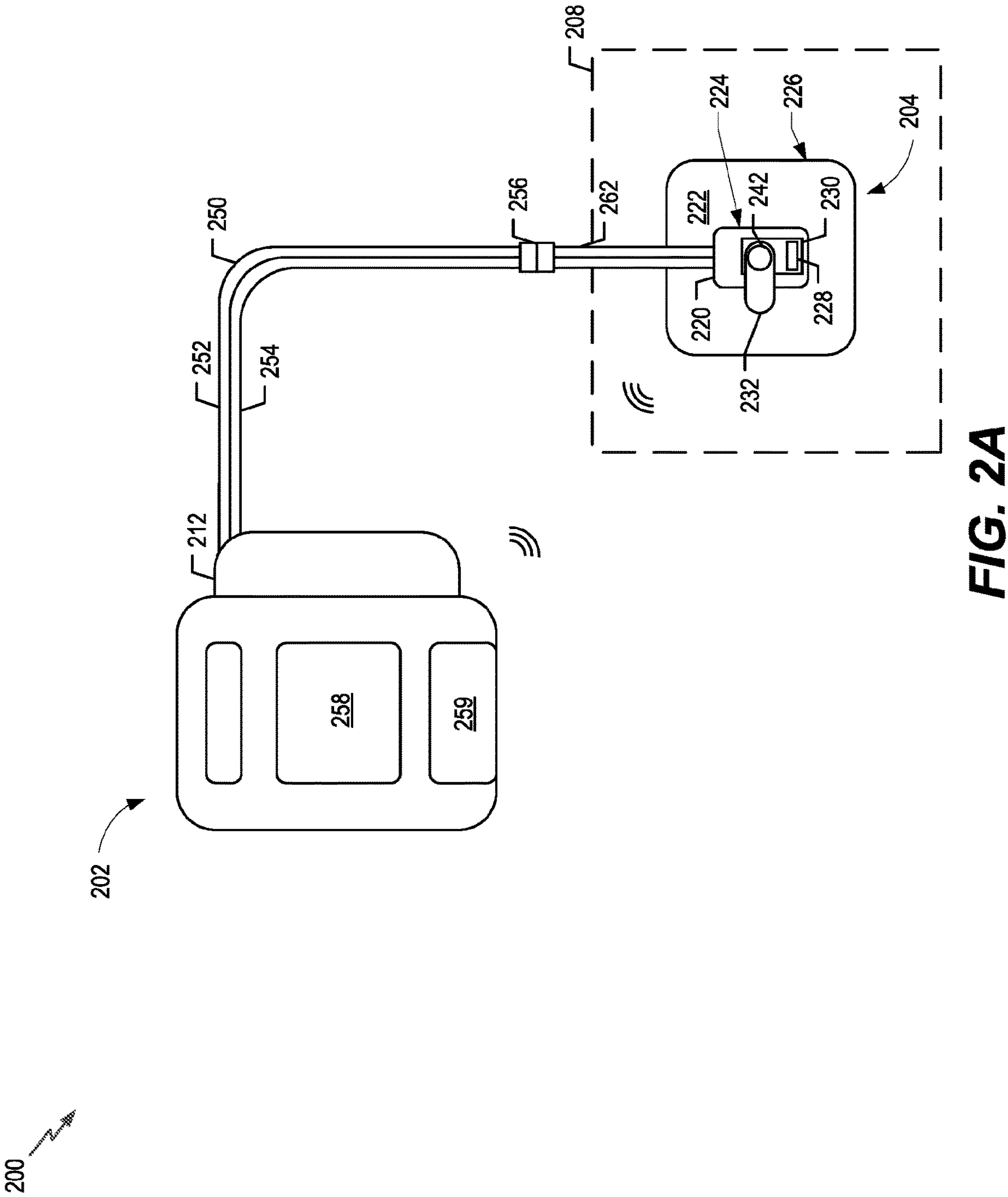
FIG. 2A is a schematic view of a first implementation of the light switchable adhesive therapy system.

In some implementations, as described further with reference to FIG. 2A, pad 120 may be configured to deliver the light from light source 128 to decouple drape 122 from tissue site 108. To illustrate, once pad 120 is decoupled from drape 122, pad 120 may be used to direct the light to first light switchable adhesive 124 that couples drape 122 to tissue site 108 of a patient. Accordingly, by using the wound dressing to direct the light, the wound dressing may have a reduced amount of layers, be easier to wear, and be easier to remove, as compared to wound dressings which are switched by remote light sources and/or are switched while the pad is attached to the drape.

As shown in FIG. 1, dressing 104 may optionally include a processor 130, a memory 132 (e.g., a computer-readable storage device), and a transceiver 134. Processor 130 may be electronically, or physically, coupled to memory 132 and transceiver 134. Each of processor 130, memory 132, and transceiver 134 may be coupled to, or positioned on or in, a portion of dressing 104 (e.g., pad 120 and/or drape 122) and may operate similarly to processor 114, memory 116, and transceiver 118 as described above with respect to therapy device 102.

Wound dressing 104 may also include one or more sensor(s) 136 in some implementations. In some such implementations, sensor(s) 136 may be configured to generate data indicative of system 100. For example, sensor(s) 136 may include a pressure sensor (e.g., a pressure transducer), a temperature sensor (e.g., a thermocouple), a humidity sensor, an electrocardiography sensor, or any other sensor suitable for monitoring a patient or an environment. Sensor(s) 136 are configured to record data associated with dressing 104. Sensor(s) 136 may be electrically coupled to, or in communication with, processor 130, memory 132, and transceiver 134 to enable transmission, analysis, and/or storage of the data generated by sensor(s) 136. For example, one sensor of sensor(s) 136 may include a temperature sensor that generates and stores the temperature of tissue site 108 and is configured to transmit a notification (e.g., sensor data 138) to therapy device 102 if a temperature increases past a predetermined temperature.

Remote device 106 may be configured to communicate with therapy device 102 and/or dressing 104. Remote device 106 includes a processor 142, a memory 144 (e.g., a computer-readable storage device), and a transceiver 146. Processor 142 may be electronically, or physically, coupled to memory 144 and transceiver 146. Each of processor 130, memory 132, and transceiver 134 may operate similarly to processor 114, memory 116, and transceiver 118 as described above with respect to therapy device 102. For example, transceiver 134 may be configure to communicate with therapy device 102 and/or wound dressing 104, and processor 142 may be configured to generate control signals and/or sensor data.

In some implementations, remote device 106 may include an application 148 associated with therapy device 102, wound dressing 104, providing therapy, or a combination thereof. For example, application 148 may include data, thresholds, and/or instructions configured to control operation of therapy device 102, wound dressing 104, or a combination thereof. Application 148 may be configured to transmit and receive instructions or commands to/from therapy device 102 and dressing 104, such as securely transmit and receive data.

Application 148 may include a user interface configured to generate and send control signals (e.g., 150, 152) responsive to receiving one or more user inputs via the application 148. In an illustrative, non-limiting example, remote device 106 may be a smart phone and application 148 may be downloaded and operated with a patient ID to monitor a specific dressing (e.g., 104) coupled to a patient. In another example, remote device 106 may be a computer or network associated with a care facility and application 148 may be a computer implemented program configured to track and monitor one or more therapy systems 100 each associated with a different patient.

Each of therapy device 102, wound dressing 104, remote device 106 may be configured to generate and/or communicate with each other via one or more control signals (e.g., 150-154), such as environment control signals, light source activation signals, pressure source control signals, or a combination thereof. For example, a processor of system 100 (e.g., 114, 130, 142) may activate and/or control light source 128 responsive to receiving an input via therapy device 102 or remote device 106 (e.g., application 148). In some implementations, the input corresponds to a code or password. In other implementations, the input corresponds to an activation signal from an user interface of application 148. In some implementations, processor (e.g., 114, 130, 142) can receive inputs (i.e., data indicating) to set a timer, delay time, activation time, etc., via interface(s) of application 148 or therapy device 102 (e.g., a wireless interface), I/O device(s), or a combination thereof. In some implementations, processor (e.g., 114, 130, 142) adjusts a power or intensity of light source 128 to control how far the emitted light travels in system 100.

In some implementations, for example, a user may access application 148 of remote device 106 to transmit a control signal 152 to transceiver 134 of wound dressing 104, which causes processor 130 to execute a command to activate light source 128. In this way, remote device 106 may be used to decouple one or more components (e.g., 120, 122) from each other or from the patient. In another illustrative, non-limiting example, processor 142 may automatically send a control signal 152 to activate light source 128 after a time exceeds a predetermined time stored in memory 144. In a further example, after receiving the control signal to activate light source 128, processor 130 of dressing 104 may prohibit execution of the instruction and send a command to transceiver 134 to transmit a control signal (e.g., 150) to remote device 106 which causes processor 142 to display a message on remote device 106 that a sufficient amount of time has not passed to enable activation of light source 128.

In some implementations, remote device 106 may transmit or receive control signal(s) 150 to therapy device 102. For example, as described above, remote device 106 may transmit a control signal 150 to therapy device 102 to activate light source 128. In another example, remote device 106 may communicate with therapy device 102 to adjust operations of pressure source 112. To illustrate, responsive to one or more signals 150 from processor 142, pressure source 112 may apply positive-pressure to dressing 104. For example, positive-pressure developed by pressure source 112 may be delivered to pad 120 or drape 122 of dressing 104. Accordingly, the pressure source 112 can increase a pressure in an interior volume of dressing 104. Internal volume (e.g., a sealed therapeutic environment) and/or tissue site 108 may be isolated from an external environment (associated with an ambient pressure).

Prior to operation of therapy device 102 or wound dressing 104, system 100 may be setup, i.e., coupled together. To illustrate, one or more components of system 100 may be provided individually and can be combined with each other to form system 100 or system 100 can be provided as a disassembled kit (e.g., kit 1000) which is assembled by a patient or a care provider (referred to herein as a user or operator).

During operation, therapy is provided by therapy device 102 to the patient via the wound dressing. For example, therapy device 102 may provide and adjust therapy based on sensor data 138, control signals (e.g., 150-154), or a combination thereof. After operation, one or more components of system 100 may be removed and/or disassembled. As an illustrative, non-limiting example, wound dressing 104 is disassembled and detached from the patient in stages, as described further herein. A new wound dressing (e.g., 104), may be coupled to patient and therapy device 102.

Referring to FIG. 2A, an example of an illustrative system 200 (e.g., a light switchable adhesive therapy system) is shown. System 200 includes a therapy device 202 (e.g., a positive-pressure or a negative-pressure therapy apparatus), at least one tube 250, and a dressing 204. Dressing 204 is coupled to therapy device 202 via the at least one tube 250. Therapy device 202 and dressing 204 may include or correspond to device 102 and dressing 104, respectively.

In some implementations, one or more tubes (e.g., 250) may be configured to couple therapy device 202 to dressing 204 or a single composite tube which includes one or more tubes or lumens may be configured to couple therapy device 202 to dressing 204. As illustrated in FIG. 2A, system 200 includes two tubes, i.e., a first tube 252 and a second tube 254. As shown, first tube 252 and second tube 254 are configured to couple to therapy device 202 to dressing 204 via connector 256, and optionally tubes 262.

In other examples, system 200 may include one tube 252 or more than two tubes 252. As illustrated in the example of FIG. 2A, tubes 262 are coupled to pad 220 of dressing 204. Pad 220 may be formed integrally with dressing 204, or may be coupleable with dressing 204. In other implementations, tube 252, tubes 254, or both, may be coupled to ports recessed in therapy device 202 or dressing 204 or fixed to (e.g., formed integrally with) therapy device 202 or dressing 204.

As used herein, a "tube" broadly refers to a tube, pipe, hose, conduit, or other structure with one or more lumens adapted to convey fluid, exudate, and/or the like, between two ends. In some implementations, a tube may be an elongated, cylindrical structure with some flexibility; however, a tube is not limited to such a structure. Accordingly, tube may be understood to include multiple geometries and rigidities.

One or more tubes 250 include one or more lumens (e.g., one or more through conduits), such as a single lumen conduit or multiple single-lumen conduits. One or more tubes 250 (e.g., a least one of the one or more lumens thereof) are configured to enable fluid communication between therapy device 202 and dressing 204. For example, fluid(s) and/or exudate can be communicated between therapy device 202 and dressing 204, and/or one or more pressure differentials (e.g., negative-pressure, positive-pressure, or both) can be applied by therapy device 202 to dressing 204. As an illustrative, non-limiting illustration, one or more tubes 250 are configured to transport (e.g., remove) fluid from dressing 204 to pressure source 212 to establish negative-pressure. Communication of fluid(s) and application of a pressure differential can occur separately and/or concurrently. As shown in FIG. 2A, each tube 250 may include one or more connection points (e.g., connectors 256). Connection points may couple components, or subcomponents, of system 200 to each other. In some implementations, a connection point couples one end of a tube (e.g., 252) to a component and the other end of the tube to a separate tube (e.g., 262). Connector(s) 256 may be coupled to tubes or together in any suitable fashion such as a mechanical connection and/or an adhesive (e.g., LSA) to fluidly couple the tubes of system 200.

In some implementations, one or more tubes of system 200 may include multiple lumens, such as a primary lumen (e.g., a pressure/fluid lumen) for application of a first pressure differential (e.g., negative-pressure) and/or communication of fluid, and one or more secondary lumens proximate to or around the primary lumen. The one or more secondary lumens (e.g., one or more ancillary/peripheral lumens) may be coupled to one or more sensors (of therapy device 202), coupled to one or more valves, as an illustrative, non-limiting example. For example, at least one secondary lumen may be a dedicated lumen (e.g., an optical lumen, a waveguide lumen, etc.) configured to transport light. One or more tubes of system 200 may include of a transparent (e.g., clear) plastic tube, a colored tube (e.g., a colored polymer tube), a fiber optic cable, a high refractive material, and/or any other suitable material to allow fluid and/or light communication from therapy device 202 to dressing 204.

Therapy device 202 may include an interface 258 and/or I/O device(s) 259. As illustrated in FIG. 2A, the interface 258 is a user interface, such as a display or a touch screen. Additionally, or alternatively, interface 258 may include a wired interface, a wireless interface, or both. In some implementation, the one or more interfaces 258 may include a network interface and/or a device interface configured to be communicatively coupled to one or more other devices (e.g., 204, 106). Interface 258 may communicate with transceiver 118 and may enable wired communication, wireless communication, or a combination thereof. Additionally, or alternatively, interface 258 may include serial interfaces (e.g., universal serial bus (USB) interfaces or Institute of Electrical and Electronics Engineers (IEEE) interfaces), parallel interfaces, display adapters, audio adapters, and other interfaces.

As illustrated in FIG. 2A, the one or more I/O devices 259 include a button. The one or more I/O devices 259 may include a mouse, a keyboard, pointing devices, a display device, the camera, speakers, microphones, touch screens, other I/O devices, or a combination thereof. In some implementations, processor 214 may configured to send and/or receive data via the interface 258 and/or the I/O device(s) 259.

Dressing 204 is configured to be coupled to (e.g., adhered to) a tissue site 208 of a patient. Dressing 204 may include one or more components, such as a pad 220, a drape 222, a first LSA 224, a second LSA 226, a light source 228, a printed circuit board ("PCB") 230, and an activator 232. Pad 220, drape 222, first LSA 224, second LSA 226, and light source 228 may include or correspond to pad 120, drape 122, first LSA 124, second LSA 126, and light source 128, respectively. As shown in FIG. 2A, PCB 230 may include processor (e.g., 130), memory (e.g., 132), transceiver (e.g., 134), and sensor(s) (e.g., 136) and may be positioned on dressing 204 (as described in more detail with reference to FIG. 3).

As shown, drape 222 may be coupled to tissue site 208 via first LSA 224. Light source 228 may be coupled to pad 220 and/or drape 222 and configured to activate first LSA 224. In some implementations, light source 228 may be positioned on dressing 204 such that light source 228 is configured to emit a light that activates a majority to all of first LSA 224 to easily decouple drape 222 from tissue site 208. For example, first LSA 224 may extend about a periphery of drape 222 and one or more light sources (e.g., 228) may be positioned along the periphery such that at least a majority of the LSA is exposed to a light emitted by the one or more light sources when the light source(s) are activated. In this manner, drape 222 may be easier to completely remove from a patient than alternative LSA bandages.

In some implementation, pad 220 is configured to be coupled to drape 222 via second LSA 226 while drape 222 is coupled to tissue site 208 via first LSA 224. Light source 228 may be coupled to pad 220 and configured to emit a light that activates second LSA 226. For example, light source 228 may be positioned such that the light emitted by light source 228 activates a majority to all of second LSA 226 to easily decouple pad 220 from drape 222. As a further example, once pad 220 is decoupled from drape 222, pad 220 may be used to direct the light to second LSA 224. Alternatively, a care provider may examine a tissue site 208 and/or target tissue, replace an absorbent material (e.g., a manifold, an insert, or other material), or other operation before recoupling pad 220 to drape 222 and resuming the wound therapy.

PCB 230 may include or be coupled to one or more electronic components, such as a processor, a memory, a transceiver, a sensor, a power source 242, etc., or a combination thereof, as illustrative, non-limiting examples. Activator 232, such as an activation means, is configured to activate the light source 228. Activator 232 may include a switch, a button, etc. As illustrated in the example of FIG. 2A, the activator 232 is a pull-tab. Pulling or removing the pull-tab activates light source 228. Activation of light source 228 causes light to be provided to at least first LSA 224. In some implementations, activation of the light source 228 (e.g., removing the pull-tab) causes light to be provided to the second LSA 226, such as after or removal of the pad 220 or prior to removal of the pad 220.

Figure 2C:
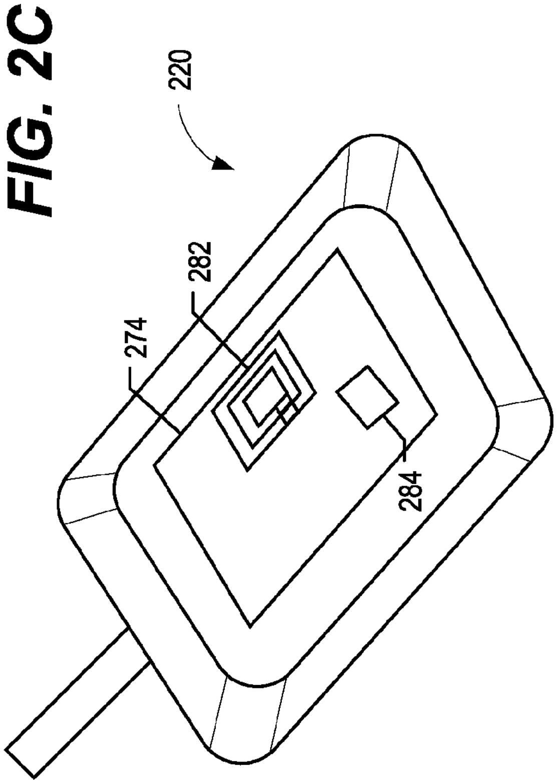
FIG. 2B-2C are each a schematic view of a pad of the therapy system of FIG. 2A.
Figure 2B:
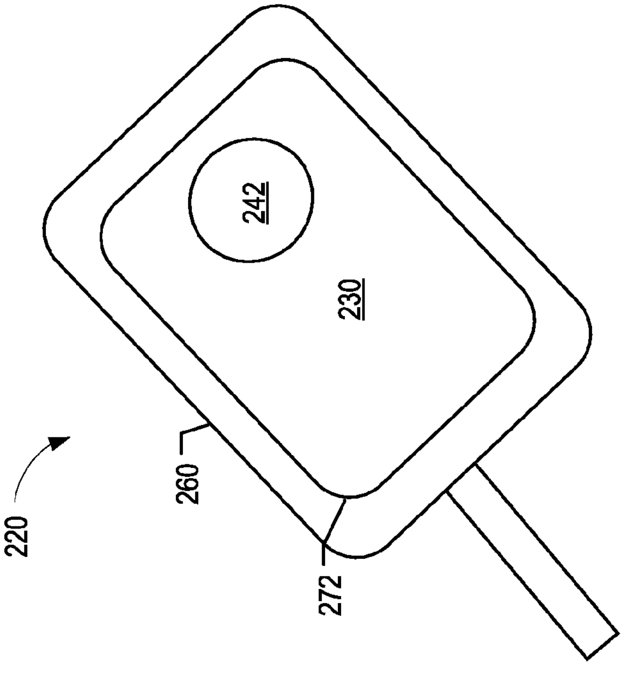

Referring now to FIGS. 2B and 2C, an implementation of pad 220 is shown. FIG. 2B illustrates a first top perspective view of pad 220, and FIG. 2C illustrates a second top perspective view of pad 220. Both FIGS. 2B and 2C illustrate schematic views of pad 220 and illustrate components which are inside of pad 220. In the example of FIGS. 2B and 2C, FIG. 2B illustrates bottom components or components which are located between top components and a tissue site when the pad 220 is coupled to the tissue site.

As illustrated in the example of FIGS. 2B and 2C, pad 220 includes a body 260 that has one or more layers. As shown in FIGS. 2B and 2C each layer may include one or more electronic components (e.g., PCB 230) configured to be operable with system 100 or 200 (e.g., a light switchable adhesive therapy system). For example, one or more layers may include or correspond to a PCB or a printed circuit board assembly ("PCBA"). To illustrate, body 260 may include a first layer 272 that includes one or more light sources 228, an operating device (e.g., integrated circuit, MOSFETs, transistor, FPGA chip, microprocessor, logic board, and/or the like), power source 242 (e.g., battery, etc.), sensor(s), or a combination thereof. As shown, power source 242 may be coupled to light source(s) 228 to enable delivery of the light to first LSA 224 and second LSA 226. In other implementations, power source 242 may be couple to any suitable portion of pad 220 or drape 222.

A second layer 274 may include similar or additional electrical components. For example, second layer 274 may include one or more communication devices. Communication devices may include an antenna, an inductor, a communication circuit, a transceiver, etc. or a combination thereof. In the example of FIG. 2C, second layer 274 includes a near-field communication (NFC) circuit 282 and a Bluetooth low energy (BLE) circuit 284. Electronic communication devices (e.g., 282 and/or 284) may be configured to wirelessly communicate with remote device (e.g., 106) or therapy device (e.g., 102, 202) to enable activation of light source or a pressure source.

Pad 220 may be configured to be controlled or operated from a therapy device or a remote device (e.g., 106) to perform wound therapy (e.g., NPWT). In some implementations, an operator may activate light source 228 of pad 220 with a therapy device (e.g., via interface 258 and/or the I/O device(s) 260) and/or remote device (e.g., 106, such as via application 148 thereof). In such implementations, removal or replacement of pad 220 of dressing 204 (and optionally dressing 204 from the tissue site) may be initiated locally via therapy device 202 or remotely via a remote device (e.g., 106).

In some implementations, a barrier may be placed between power source (e.g., 242) and light source 228 such that removal of the barrier will establish a connection between the power source and the light source to activate the light source. For example, the barrier may include a tab (e.g., 232) that can be pulled by an operator to initiate a connection between light source 228 and power source 242 and trigger removal of dressing 204 from patient site. Specifically, removing the tab may remove the isolation of the power source 242 from PCB 230 and/or light source 228.

Figure 3:
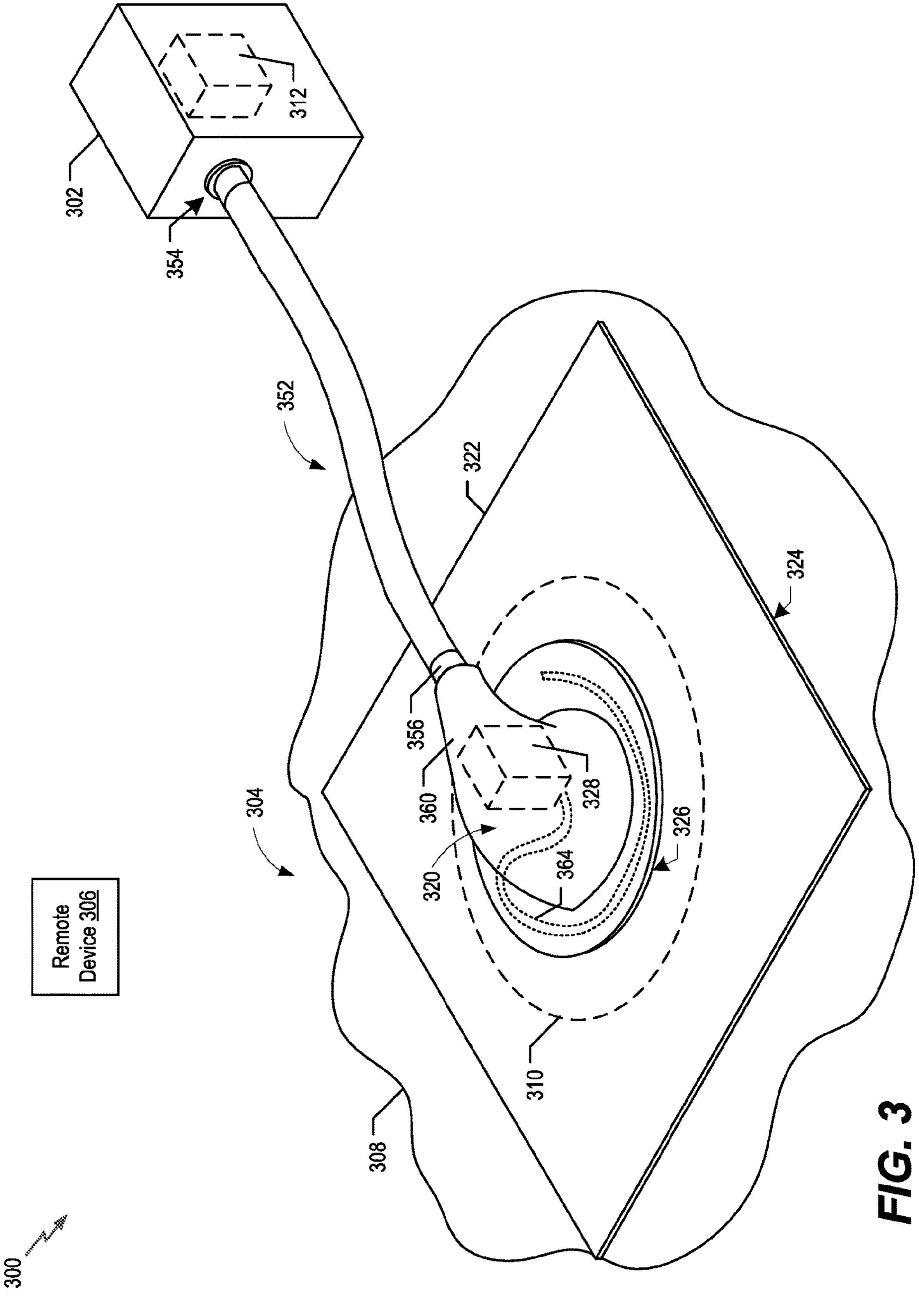
FIG. 3 is a perspective view of an example of the first implementation of the therapy system.

Referring now to FIG. 3, a perspective view of a system 300 is shown in use on a tissue site 308. System 300 may include a therapy device 302, pressure source 312, a tube 352, a dressing 304, a remote device 306, and a light source 328. System 300 is configured to provide pressure therapy (e.g., NPWT) to a tissue site 308 associated with a target area of a patient. For example, dressing 304 may be in fluid communication with tissue site 308 and may be in fluid communication with therapy device 302 via tube 352.

Therapy device 302, dressing 304, and remote device 306 may include or correspond to therapy device 102, dressing 104, and remote device 106 respectively. Pressure source 312 and tube 352 may include or correspond to pressure source 112 and one or more tubes 250 (e.g., tubes 252, 254), respectively. Therapy device 302 may include one or more sensors, such a pressure sensor (e.g., a pressure transducer). The one or more sensors may be configured to enable therapy device 302 to monitor and/or sense a pressure associated with tube 352 and/or dressing 304. In some implementations, system 300 may include one or more components commercially available through and/or from KCI USA, Inc. of San Antonio, Tex., U.S.A., and/or its subsidiary and related companies (collectively, "KCI").

System 300 may include one or connectors configured to connect components of system 300. Connectors 354, 356 may include or correspond to connector 256. As shown in FIG. 3, first connector 354 is configured to be coupled to tube 352 and therapy device 302. In some implementations, a second connector 356 is configured to couple tube 352 to dressing 304 (e.g., pad 320). In some implementations, connectors 354, 356 may be used to couple therapy device 302 and dressing 304 to any suitable external component as described herein. Additionally, dressing 304 and/or therapy device 302 may include a port configured to be coupled to connectors 354, 356.

Dressing 304 may be a two-piece removable dressing that incudes pad 320 and drape 322. For example, pad 320 may be decouplable from drape 322 independent from, or in addition to, drape 322 being decouplable from tissue site 308. As shown, drape 322 is configured to be coupled to tissue site 308 such that drape 322 covers a portion of tissue site 308. Drape 322 may be configured to couple dressing 304 at tissue site 308 and/or to provide a seal to create an enclosed space (e.g., an interior volume 310) corresponding to tissue site 308. For example, drape 322 and pad 320 may be configured to provide a fluid seal between two components and/or two environments, such as between a sealed therapeutic environment and a local ambient environment. Drape 322 may include a drape aperture that extends through drape 332 to enable fluid communication between therapy device 302 and target tissue of tissue site 308. In some implementations, pad 320 is coupled to drape 322 such that pad 320 covers drape aperture to partially define interior volume and maintain the fluid seal. As shown in FIG. 3, drape 322 is coupled to tissue site 308 via first LSA 324 and pad 320 is coupled to drape 322 via second LSA 326.

Dressing 304 (e.g., drape 322 and/or pad 320) may include an impermeable or semi-permeable, elastomeric material, as an illustrative, non-limiting example. In some implementations, drape 322 or pad 320 may be liquid/gas (e.g., moisture/vapor) impermeable or semi-permeable. "Elastomeric" means having the properties of an elastomer. For example, elastomer generally refers to a polymeric material that may have rubber-like properties. More specifically, an elastomer may typically have ultimate elongations greater than or equal to 100% and a significant amount of resilience. The resilience of a material refers to the material's ability to recover from an elastic deformation. Elastomers that are relatively less resilient may also be used as these elastomers. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane (PU), Ethylene-vinyl acetate (EVA) film, co-polyester, and silicones. In some implementations, dressing 304 may include the "V.A.C.® Drape" commercially available from KCI. Additional, specific non-limiting examples of materials of dressing 304 may include a silicone drape, 3M Tegaderm® drape, and a polyurethane (PU) drape such as one available from Avery Dennison Corporation of Pasadena, Calif. In some implementations, pad 320 may include a rigid material and/or a semi-rigid material. In a non-limiting example, pad 320 may be made from a plasticized polyvinyl chloride (PVC), polyurethane, cyclic olefin copolymer elastomer, thermoplastic elastomer, poly acrylic, silicone polymer, or polyether block amide copolymer.

In some implementations, dressing 304 may include a shroud coupled to an exterior surface of drape 322, the shroud configured to reflect the light within the dressing, block second light from entering the dressing, or both. Shroud is positioned such that the shroud blocks first LSA 324 and/or second LSA 326 from receiving light, such as ambient light. In some implementations, shroud is formed of or includes a material that is configured to block (e.g., reflect or absorb) ambient light that would otherwise activate first LSA 324 and/or second LSA 326. Thus, shroud enables the use of ambient light and/or does not require a dedicated light device, transporting light via components of a therapy system, or both.

In some implementations, pad 320 further includes a light guide 364 which light source 328 is configured to emit light through. As illustrated in FIG. 3, light source 328 is incorporated into a body 360 of pad 320. For example, light source 328 may be incorporated within a layer of pad 320, between layers of pad 320, or within a channel defined by pad 320 such that light source 328 is configured to emit light through a portion of pad 320. To illustrate, light source 328, alone or in combination with light guide 364, one or more reflectors, refractors, collimators, lens, waveguides, etc., directs light to first LSA 324, second LSA 326, or both.

As illustrated in the example of FIG. 3, light guide 364 (e.g., a wave guide) is incorporated into pad 320 and may include one or more components configured to transport light from light source 328 to a LSA (e.g., first LSA 324, second LSA 326, or other) attached to dressing 304 (e.g., drape 322 or pad 320). In FIG. 3, light guide 364 is an optical tube or lumen incorporated, at least partially, into body 360 of pad 320 and configured to deliver light to pad 320 (e.g., a periphery, or portion of body 360 attached to second LSA 326). For example, light guide 364 may include one lumen for each LSA or portion/section of adhesive. As another example, a single light guide 364 having a single lumen transports the light, and apertures or high refractive/transmission material (e.g., diffusion material) is incorporated into light guide 364 to form a plurality of transmission elements such that light guide 364 disperses or diffuses light through the single lumen into pad 320 and/or adhesive via the plurality of transmission elements.

Additionally, or alternatively, light guide 364 is incorporated into drape 322. In a particular implementation, light guide 364 is a fiber optic cable. In some implementations, light guide 364 may include one or more lumens to transport the light. Although light guide 364 is illustrated in FIG. 3 along with light source 328 are incorporated into pad 320, other implementations described herein can incorporate a light guide, such as light guide 364 and/or light source 328 within therapy device 302, tube 352, or other component of system 300 to transport/deliver light to LSA. To illustrate, in implementations where light source 328 is incorporated into therapy device 302 or is delivered to dressing 304 via one or more tubes, light guide 364 may be coupled to pad 320 to receive the light and to transport and deliver the light to the LSAs which couple the pad 320 to drape 322 or drape 322 to tissue site 308. Illustrative, non-limiting examples of commercially available connectors include a "V.A.C. T.R.A.C.® Pad," or "Sensa T.R.A.C.® Pad" available from Kinetic Concepts, Inc. (KCI) of San Antonio, Tex.

After completion of wound therapy or when replacing a component of system 300, light source 328 may be coupled directly to dressing 304 (e.g., pad 320) and activated to provide a light to dressing 304, and optionally connection points between other components of system 300. To illustrate, in a non-limiting example, light source 328 emits UV light into light guide 364. Light guide 364 receives the UV light and transports the UV light through pad 320 and body 360 to drape 322 and first LSA 324. In a particular implementation, light guide 364 delivers light to drape 322 via a plurality of transmission elements along a length of light guide 364. In some implementations, drape 322 receives the light and diffuses (or further diffusers the light) to deliver the light to first LSA 324. The UV light causes the LSA to transition from a higher tack state to a lower tack state and/or transition from a high peel strength state to a lower peel strength state which facilitates easy pain and trauma free removal of adhesive and dressing 304 from tissue site 308. In this manner, removal or replacement of system 300 may be performed quickly and effectively without the need for additional external components.

In an alternative implementation, light source 328 may be coupled directly to dressing 304 (e.g., pad 320) and activated to provide a light to dressing 304, and optionally connection points between other components of system 300 Light source 328 emits UV light (e.g., through light guide 364). Pad 320 receives the UV light and delivers the UV light through pad 320 (e.g., via body 360 or light guide 364) to second LSA 326. The UV light causes the LSA to transition from a high-tack state to a low-tack state and facilitates easy removal of second LSA 326 and pad 320 from drape 322. After removal pad 320 may be used to facilitate removal of drape 322 (e.g., directing pad 320 to provide the UV light to first LSA 324) as explained in greater detail with reference to FIGS. 4A and 4B, below.

Thus, a light source 328 can be integrated into dressing 304 (e.g., pad 320) of a system including LSA to provide easy removal or replacement of a dressing (e.g., 304) used in NPWT treatment. In some implementations, dressing 304 may be disposable to hinder or prevent reuse of single-use components to reduce infection and contamination. By providing a light source (e.g., 328) incorporated into dressing 304, a producer can minimize the risk of a patient losing or damaging any external components. Additionally, system 300 (e.g., one or more of the components thereof) can be configured to allow disconnection of dressing with a low disconnection force such that the young, elderly, and sick may easily connect and disconnect the devices and systems.

Figure 4A:
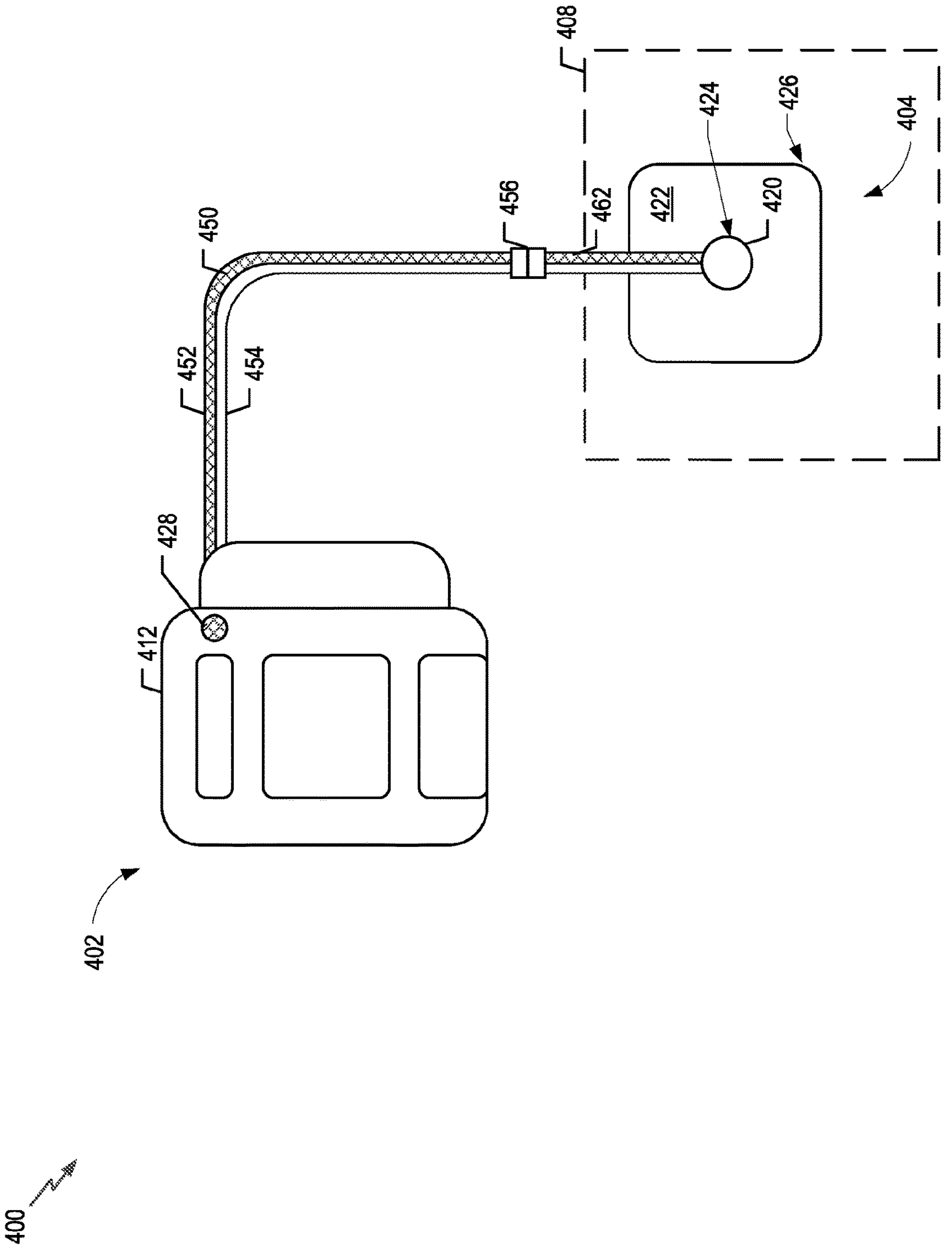
FIG. 4A-4B are schematic views of a second implementation of the light switchable adhesive therapy system.
Figure 4B:
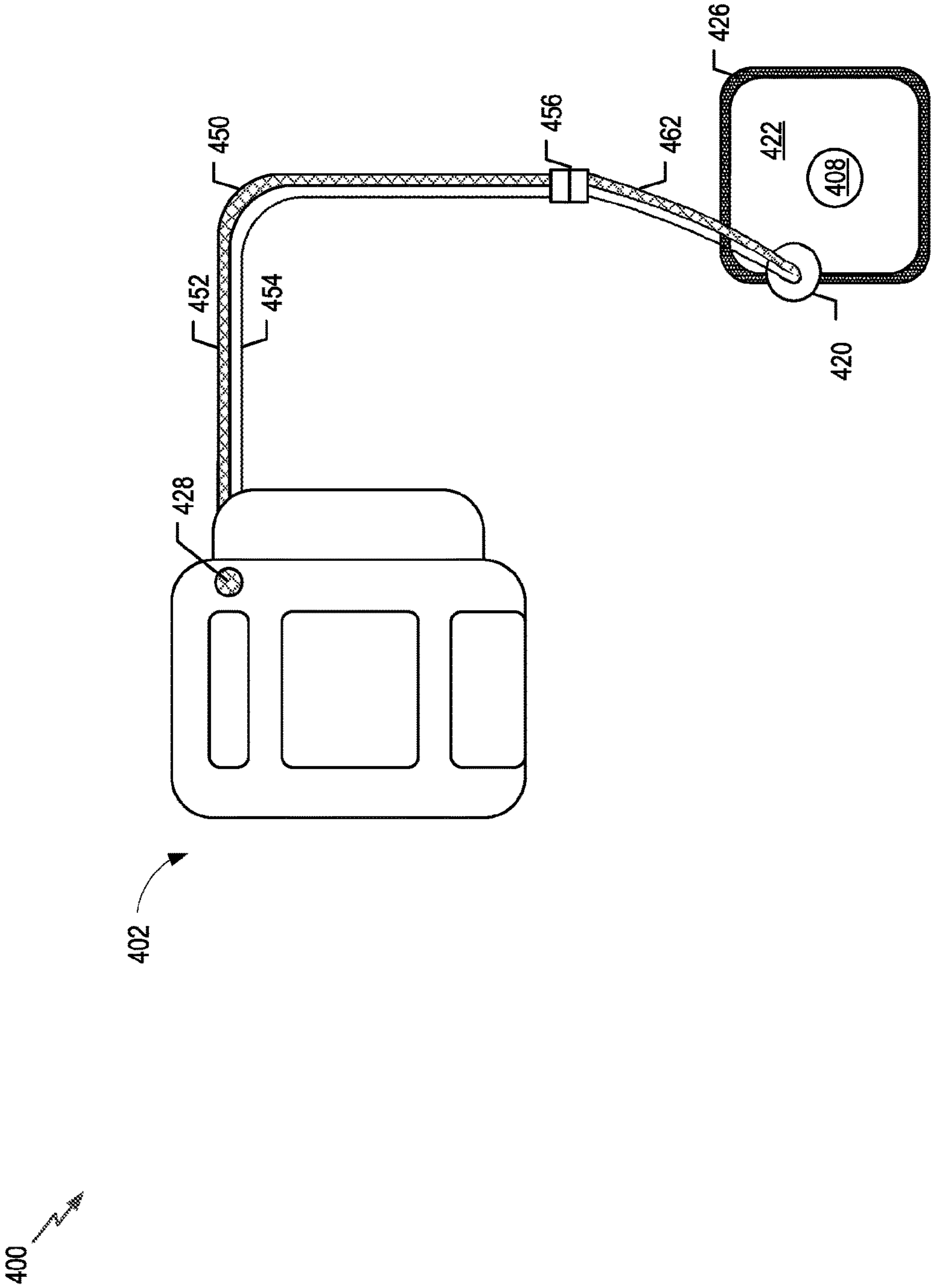

Referring now to FIGS. 4A and 4B, an illustrative example of a therapy system 400 (e.g., a negative or positive pressure wound therapy system) is shown. FIG. 4A illustrates a top schematic view of system 400 prior to activation of a light source, and FIG. 4B illustrates a top schematic view of system 400 after to activation of a light source.

System 400 includes a therapy device 402 (e.g., a positive-pressure or a negative-pressure therapy apparatus), tube 450, and a dressing 404. Dressing 404 may be coupled to device 402 via one or more tubes 450. Therapy device 402 and dressing 404 may include or correspond to therapy device 102 and dressing 104, respectively. One or more tubes 450 may include or correspond to tube(s) 250 and include one or more connectors 454 that correspond to connectors 256 of FIG. 2A.

Dressing 404 may be a two-piece removable dressing that includes a pad 420 and a drape 422. Pad 420 and drape 422 may include or correspond to pad 120 and drape 122. As shown, pad 420 may be decouplable from drape 422 independent from, or in addition to, drape 422 being decouplable from a tissue site 408. For example, drape 422 is couple to tissue site 408 via a second LSA 426 and pad 420 is coupled to drape 422 via a first LSA 424.

Dressing 404 is configured to receive light from light source 428 (e.g., a distinct UV device separate from dressing 404). For example, pad 420 is configured to couple (e.g., optically couple) light source to drape 422 (e.g., via a light guide, such as 364). As another example, dressing 404 may include one or more windows which enable light generated by light source 428 to pass through to first LSA 424, second LSA 426, or light guide. The one or more windows may be protected by a cover film or shroud when light source 428 is not in use. In some implementations, light source may be positioned in therapy device 402 and configured to deliver light through tubes 450 to dressing 404. For example, as shown in FIGS. 4A and 4B, light source 428 is disposed in therapy device 402 and tubes 452 (e.g., tube 452, 462) defines an optical pathway between therapy device 402 and dressing 404.

After completion of wound therapy or when replacing a component of system 400, light source 428 may be coupled upstream from dressing 404 (e.g., pad 420 and drape 422) and activated to provide a light to dressing 404, and optionally connection points between other components of system 400. To illustrate, in a non-limiting example, light source 428 emits UV light through tubes 450, 462 and connectors 456. Pad 420 receives the UV light and transports the UV light through pad 420 to a first LSA 424 (e.g., via a light guide or other transmission elements). In some implementations, pad 420 receives the light and diffuses (or further diffusers the light) to deliver the light to first LSA 424. The UV light causes the first LSA 424 to transition from a high-tack state to a low-tack state and facilitates easy removal of pad 420 from drape 422. In this manner specialized removal or replacement of components of dressing 404 may be achieved without removal of the entire dressing 404. This may help reduce fatigue on tissue site 408 when replacement or removal of dressing 404 is required multiple times during treatment.

As an illustrative, non-limiting illustration, removal of pad 420 may give an operator access to tissue site 408 without having to remove drape 422. For example, pad 420 may cover an opening defined by drape 422 where an absorbent material is placed, and once pad 420 is decoupled from drape 422, the absorbent material may be replaced without the removal of drape 422. Access to tissue site 408 without removal of drape 422 may be desirable when tissue site 408 is sensitive to even gentle contact (e.g., peel strength of a conventional bandage). In some implementations, a new pad or therapy device may be connected to drape 422 or pad 420 may be reconnected to drape 422.

Further, after removal, pad 420 may be used to facilitate removal of drape 422. Pad 420 is coupled to tube 462 to receive the light from light source 428. Pad 420 is then configured to direct the light and is moveable relative to drape 422 to activate second LSA 426 to decouple drape 422 from tissue site 408. In some implementations, pad 420 may be used to selectively decouple a portion of drape 422 without removal of the entire drape 422. In other implementations, pad 420 may be configured to direct light to second LSA 426 to facilitate quick removal of drape 422. Pad 420 may be designed to easily access portions of drape 422 where second LSA 426 is adhered. For example, removing pad 420 may also expose an opening defined by drape 422 to obtain greater access to second LSA 426. As illustrated in FIG. 4B, when pad 420 is removed from drape 422, tissue site 408 may be exposed through drape 422.

Figure 5A:
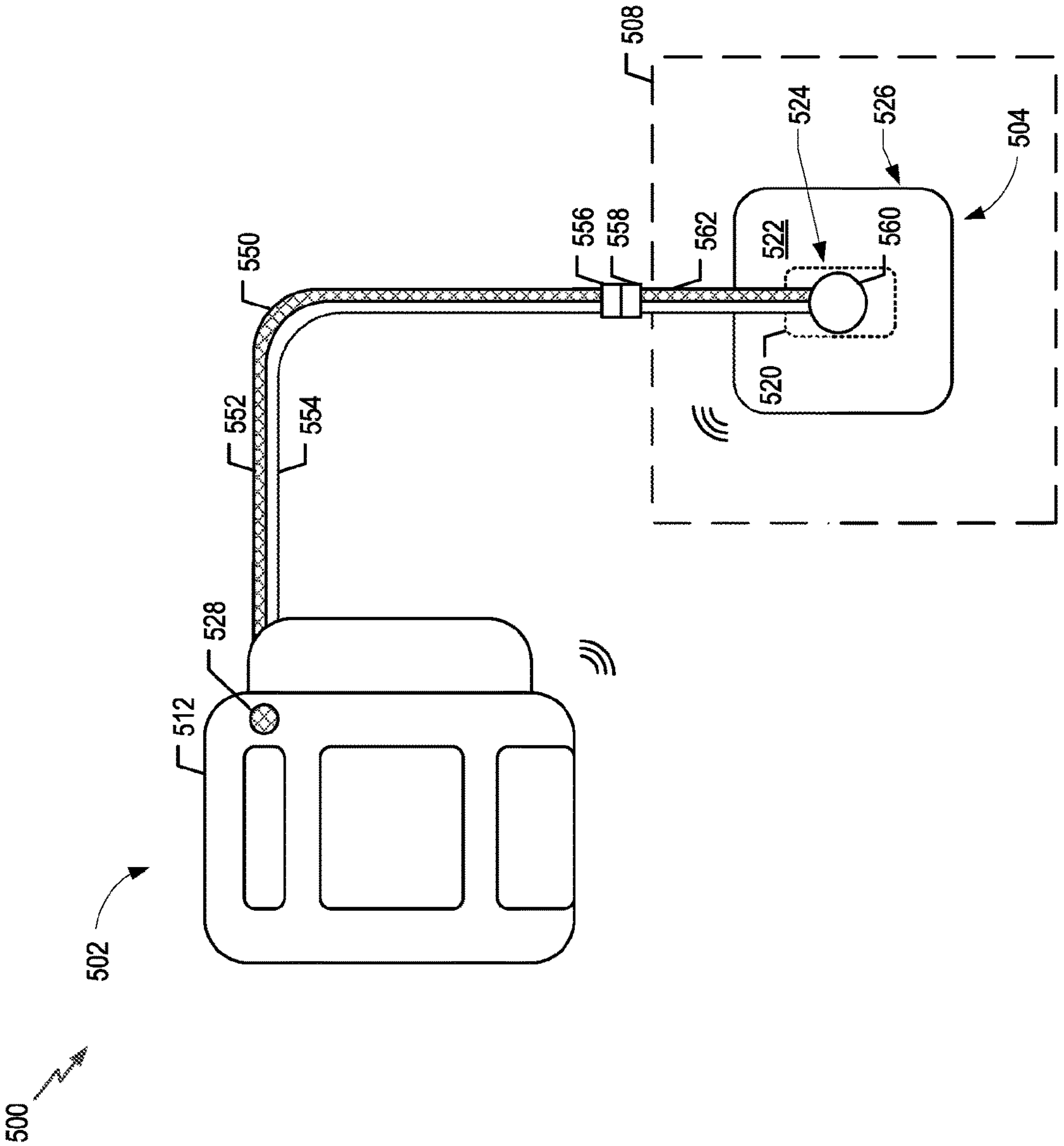
FIG. 5A-5B are schematic views of a third implementation of the light switchable adhesive therapy system.
Figure 5B:
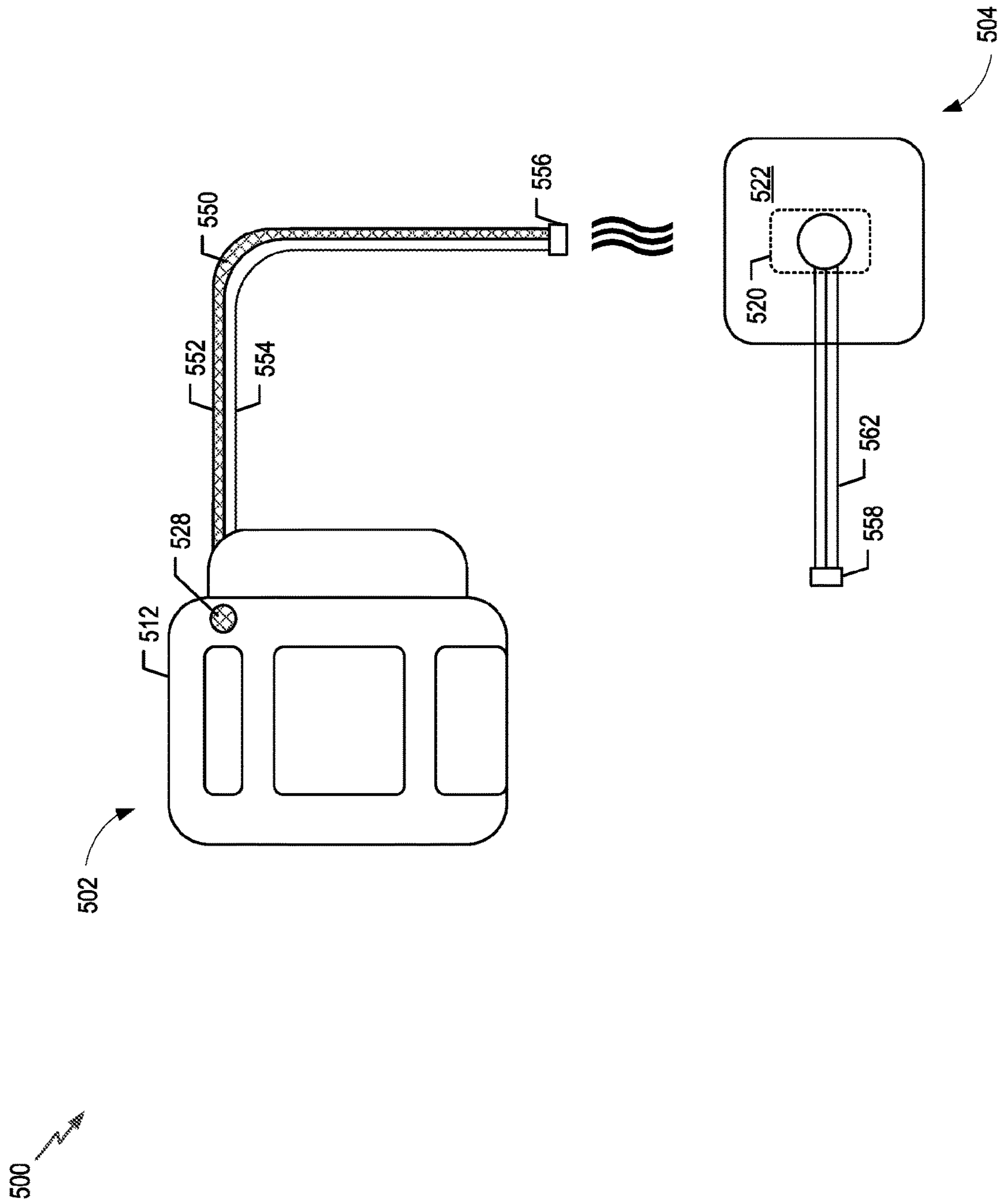

Referring now to FIGS. 5A and 5B, another implementation of system 500 is shown. System 500 includes a therapy device 502 (e.g., a positive-pressure or a negative-pressure therapy apparatus), one or more tubes 550, and a dressing 504. Dressing 504 may be coupled to device 502 via one or more tubes 550. Therapy device 502 and dressing 504 may include or correspond to therapy device 102 and dressing 104, respectively. One or more tubes 550 may include or correspond to tube(s) 550 and include one or more connectors 556 that correspond to connectors 256 of FIG. 2A.

System 500 includes similar components to system 400. As compared to system 400, which uses pad 420 to direct light, in system 500 a connector, such as connector 556, is used to direct light from a light source, such as light source 528, upstream of the dressing 504.

As described above, light source 528 may be coupled upstream from dressing 504 (e.g., pad 520 and drape 522), included in therapy device 502 as illustrated in FIG. 5A, and activated to provide a light to dressing 504, and optionally connection points between other components of system 500. To illustrate, in a non-limiting example, light source 528 emits UV light tubes 552, 554. A connector 556 receives the UV light and emits the light via an opening or aperture thereof when disconnected from dressing 504, such as from connector 558.

In some implementations, connectors 556 and 558 are mechanically connected and can be mechanically disconnected to provide light to dressing 504, or at least a portion thereof, such as an exterior thereof to deactivate second LSA. Additionally, or alternatively, a third LSA may be used, similar to first or second LSAs described herein. The third LSA may be configured to couple the connectors 556, 558 together or the connector 556 to another component. Activation of the light source 528 may switch/deactivate third LSA, enabling decoupling of connector 556 from the other component, that is connector 558 in the example of FIGS. 5A and 5B. Accordingly, after decoupling, the connector 556 and/or tubes 552, 554 may be used to direct light. In some implementations, pad 520 may be replaced with a new pad without removal of the entire dressing 504. In this manner connectors may be designed to facilitate quick removal of dressing 504 that is customizable to the patient's specific needs and conditions.

Figure 6:
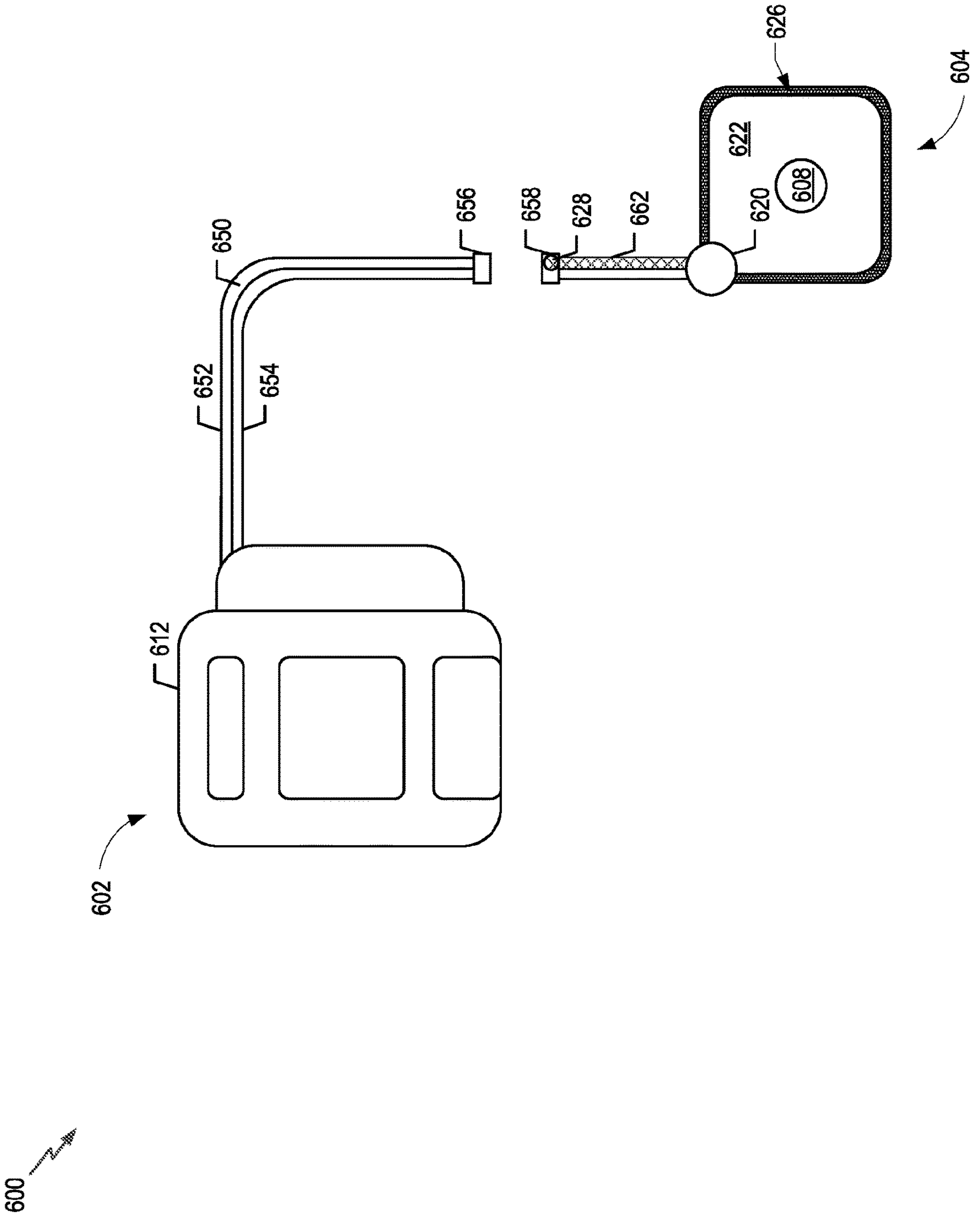
FIG. 6 is a schematic view of a fourth implementation of the light switchable adhesive therapy system.

Referring now to FIG. 6, an illustrative example of a therapy system 600 (e.g., a negative or positive pressure wound therapy system) is shown. System 600 includes a therapy device 602 (e.g., a positive-pressure or a negative-pressure therapy apparatus), one or more tubes 650, and a dressing 604. Dressing 604 may be coupled to device 602 via one or more tubes 650. Therapy device 602 and dressing 604 may include or correspond to therapy device 102 and dressing 104, respectively. One or more tubes 650 may include or correspond to one or more tubes 250 and include one or more connectors 656, 658 that correspond to connectors 256.

Dressing 604 may be a two-piece removable dressing that includes a pad 620 and a drape 622. Pad 620 and drape 622 may include or correspond to pad 120 and drape 122. As shown, pad 620 may be decouplable from drape 622 independent from, or in addition to, drape 622 being decouplable from a tissue site (e.g., 208). For example, drape 622 is couple to tissue site via a first LSA 624 and pad 620 is coupled to drape 622 via a second LSA 626. One or more tubes 652, 654 may couple dressing 604 to therapy device 602, such that at least one of the tubes 652 defines an optical pathway between therapy device 602 and dressing 604. As illustrated in FIG. 6, when pad 620 is removed from drape 622, tissue site 608 may be exposed through drape 622.

In some implementations, light source 628 may be positioned in a portion of a tube or a connector of system 600. For example, light source 628 may be coupled to a connector 658 of tube(s) 662. Specifically, in a non-limiting example, light source 628 may be coupled to connector 658 where tube(s) 662 connects to tube 652, 654. To illustrate, in a non-limiting example, light source 628 emits UV light through at least a portion of a tube (e.g., 662) and to dressing 604.

In some implementations, a power source may be positioned within the connector or the tube. In other implementations, the power source is positioned in the therapy device or dressing and is coupled to the light source 628.

After activation of light source 628, a tube (e.g., 662) may then be used to direct light from the light source 628 to dressing 604. As shown in FIG. 6, pad 620 may be decoupled from drape 622 and the pad 620/tube 662 may be used to direct the light to other portions of dressing 604. In this manner, pad 620 may be smaller than that of pad 220 as light source 628 and power source 630 are not housed in dressing 604, such as housed in a connector. This may allow for pad 620 to direct light to hard to reach places where first LSA 624 is adhered to drape 622. Additionally, tube 662 may be moved independently of therapy device 602 to allow for greater control of pad 620. It is noted that one or more operations described with reference to systems of FIGS. 1-6 may be combined with one or more operations of another of FIGS. 1-6. For example, one or more components of system 200 may be combined with one or more components of systems 400 or 600.

Figure 7:
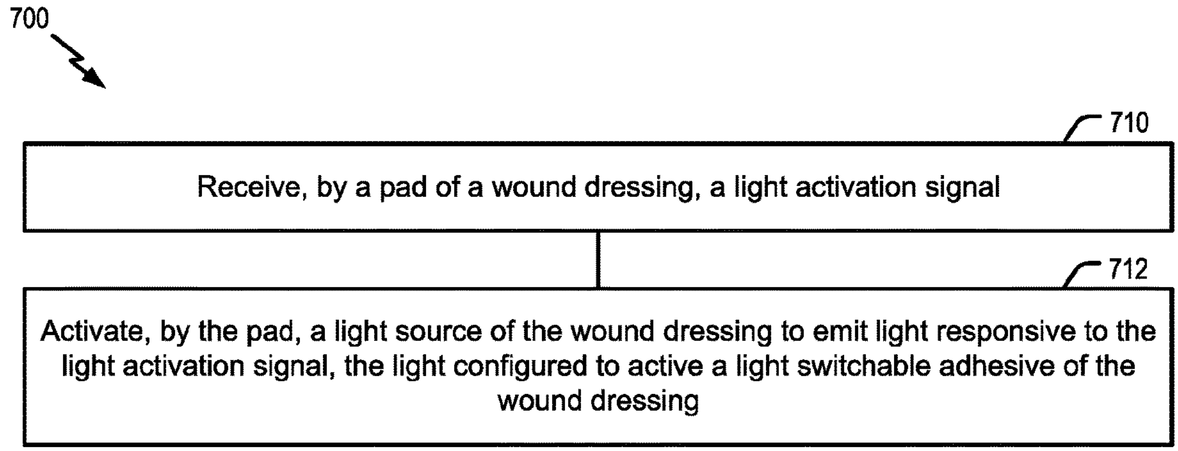
FIG. 7 is a flowchart illustrating an example of a method of using the therapy system.

FIG. 7 illustrates a method of operating a therapy system. The method 700 may be performed at, by, or with system 100 (e.g., one or more components thereof), a system that includes a therapy device 102, a wound dressing 104, a remote device 106, and a light source 128, the system 200 (e.g., one or more components thereof), or the system 400 (e.g., one or more components thereof. Method 700 includes receiving, by a pad (e.g., 102) of wound dressing 104 a light activation signal, at 710. Method 700 further includes activating, by the pad, a light source (e.g., 128) of the wound dressing to emit light responsive to the light activation signal, at 712. In some implementations, the light is configured to active a light switchable adhesive ("LSA") of the wound dressing. The LSA may be configured to couple the pad to the drape, or couple the drape to a tissue site (e.g., 108).

In some implementations, method 700 further includes directing, by the pad, the light to a first light switchable adhesive. For example, method 700 may include moving the pad to direct the light from the light source. In response to being moved, method 700 may include directing, by the pad, the light source to a second light switchable adhesive. In some implementations, the first LSA is configured to couple the pad to the drape and the second LSA is configured to couple the drape to a tissue site. In some implementations, method 700 further includes receiving the light activation signal at a controller of the pad prior to activating the light source by the controller.

Figure 8:
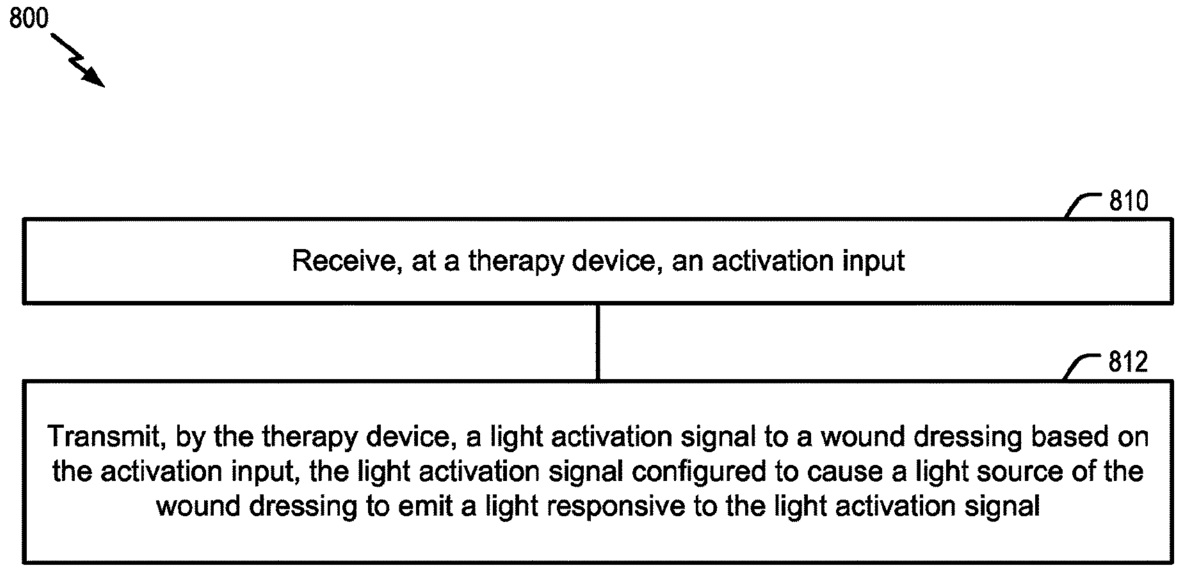
FIG. 8 is a flowchart illustrating another example of a method of using the therapy system.

FIG. 8 illustrates a method of operating a therapy system. The method 800 may be performed at, by, or with system 100 (e.g., one or more components thereof), a system that includes a therapy device 102, a wound dressing 104, a remote device 106, and a light source 128, the system 200 (e.g., one or more components thereof), or the system 400 (e.g., one or more components thereof. Method 800 includes receiving, at a therapy device (e.g., 102), an activation input, at 810. Method 800 further includes transmitting, by the therapy device, a light activation signal (e.g., 150) to a wound dressing (e.g., 104) based on the activation input. In some implementations, the light activation signal is configured to cause a light source (e.g., 128) of the wound dressing to emit a light responsive to the light activation signal, at 812.

In some implementations, method 800 further includes setting a timer associated with the light activation signal, wherein the light source emits the light responsive to expiration of the timer. In some implementations, receiving the activation input includes receiving the activation input from a remote device (e.g., 106). In other implementations, the activation input is generated at the therapy device based on a timer, or a user input. In some implementations, the therapy device and the remote device may work in conjunction to generate the activation input or the light activation signal. For example, the activation input may be generated at the therapy device based on a user input, where the user input is in a non-selectable state until activated by the remote device. In other implementations, the therapy device and the remote device may be controlled in any manner as described above.

Figure 9:
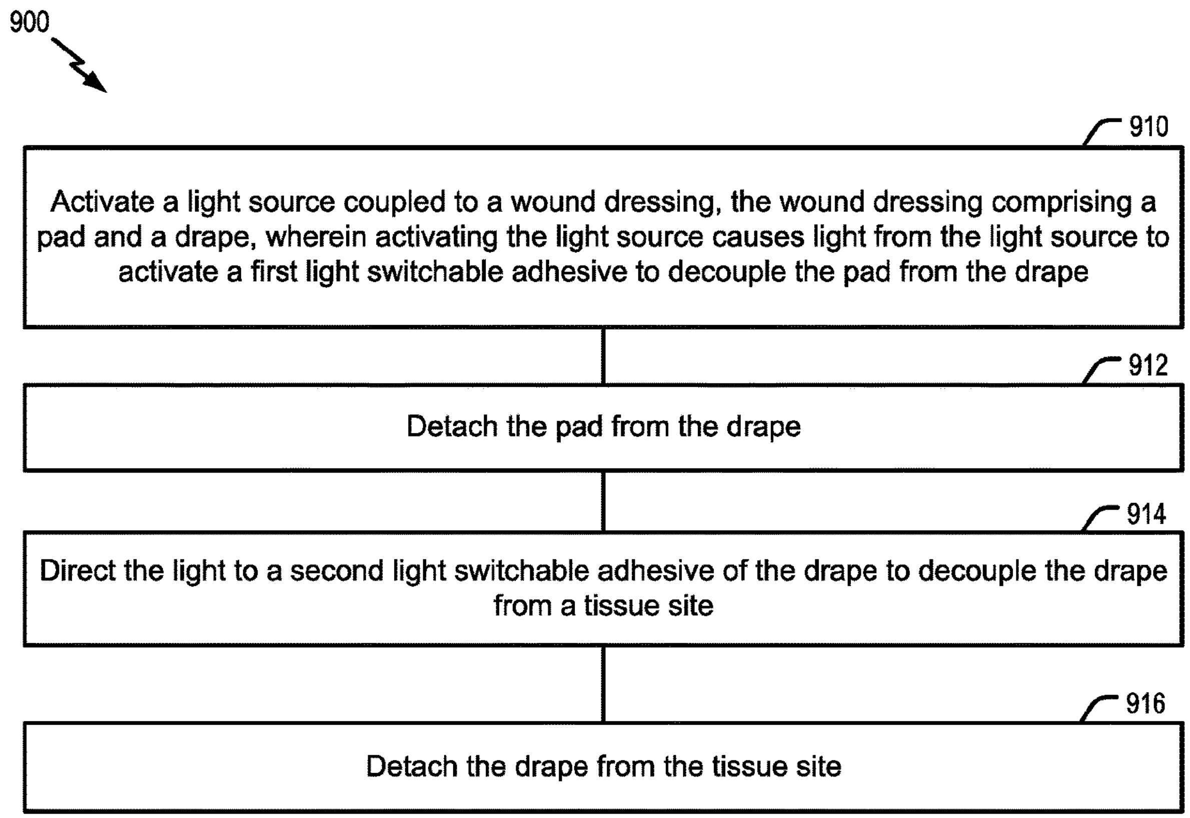
FIG. 9 is a flowchart illustrating an example of a method of using a wound dressing of the therapy system.

FIG. 9 illustrates a method of using a wound dressing of a therapy system. The method 900 may be performed at, by, or with system 100 (e.g., one or more components thereof), a system that includes a therapy device 102, a wound dressing 104, a remote device 106, and a light source 128, the system 200 (e.g., one or more components thereof), or the system 400 (e.g., one or more components thereof. Method 900 includes activating a light source (e.g., 128) coupled to a wound dressing (e.g., 104), at 910. The wound dressing may include a pad (e.g., 120) and a drape (e.g., 122). In some implementations, activating the light source causes light from the light source to activate a first LSA (e.g., 126) to decouple the pad from the drape. In some such implementations, activating a light source further includes directing the light to the first light switchable adhesive to decouple the pad from the drape, from an absorbent material, or both, of the wound dressing. The method 900 further includes detaching the pad from the drape, at 912.

In some implementations, method 900 further includes directing the light to a second LSA (e.g., 124) of the drape to decouple the drape from a tissue site (e.g., 108), at 914, and detaching the drape from the tissue site, at 916. In some such implementations, directing the light to the second LSA includes moving the pad to direct the light to the second LSA attached to the drape. Directing the light to the second LSA may activate the LSA to transition the LSA from a high-tack state to a low-tack state. In some implementations, moving the pad to direct the light further includes moving the pad relative to the drape while the drape is coupled to the tissue site. In some implementations, activating the light source may be done by a therapy device (e.g., 102), a remote device (e.g., 106), or the dressing. For example, activating the light source includes providing an input to the remote device.

Method 900 may further include attaching the wound dressing to a tissue site of a patient. In some implementations, attaching the wound dressing may include attaching at least a portion of a new wound dressing after detaching the wound dressing. For example, a new pad or a new drape may be coupled to the tissue site. In other implementations, attaching the wound dressing may include attaching the wound dressing prior to detaching the wound dressing or, in yet other implementations, attaching the wound dressing may include reattaching the wound dressing. In some implementations, method 900 includes attaching the drape to the tissue site of the patient via the second light switchable adhesive, removing a portion of the drape, and attaching the pad to the drape via the first light switchable adhesive such that the pad covers the portion of the drape.

Method 900 may further include prior to attaching, removing a cover film from the pad, the drape, or both. In some implementations, method 900 may include connecting a tube (e.g., 252) to the wound dressing. In some implementations, the tube is configured to communicate the light from the light source to the pad. In some implementations, method 900 may include connecting the therapy device to the wound dressing. The therapy device may activate the light source and in some implementations, the light source is included in the therapy device or the tube.

It is noted that one or more operations described with reference to one of the methods of FIGS. 7-9 may be combined with one or more operations of another of FIGS. 7-9. For example, one or more operations of method 700 may be combined with one or more operations of method 800 or 900. Additionally, or alternatively, one or more operations described above with reference to FIGS. 1, 2A-2C, 3, 4A-4B, 5A-5B, and 6 may be combined with one or more operations of FIG. 7, FIG. 8, FIG. 9, or a combination of FIGS. 7-9.

Figure 10:
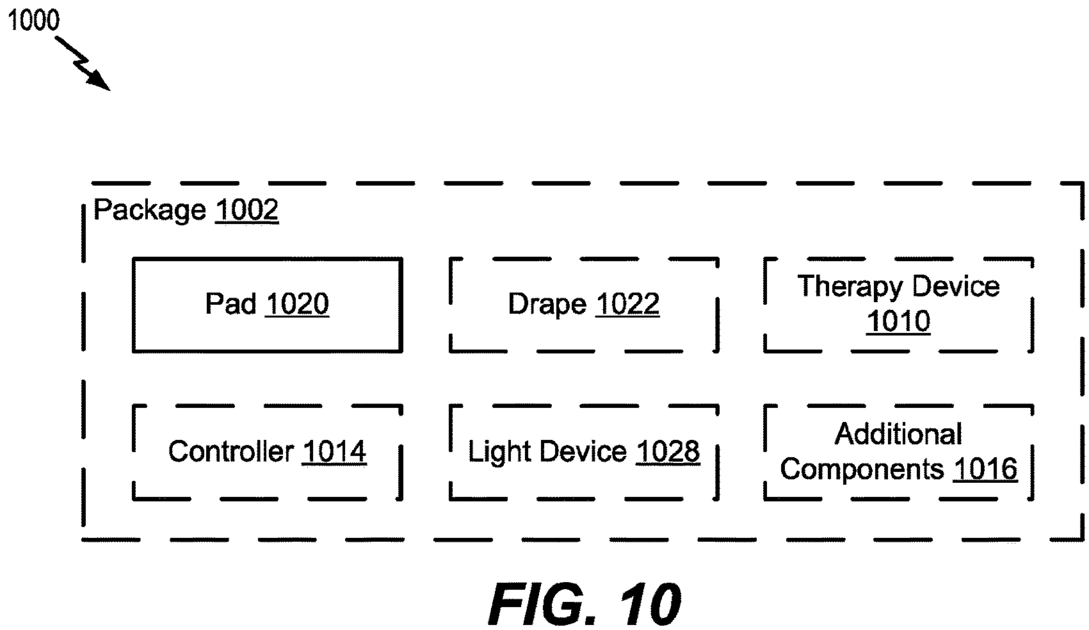
FIG. 10 is a block diagram illustrating a kit for a light switchable adhesive therapy system.

Referring to FIG. 10, a kit 1000 for therapy devices, such as a component (e.g., 104) of system 100, is illustrated. Kit 1000 includes a pad 1020 and/or a drape 1022. The pad 1020 may include or correspond to pad 120, pad 220, pad 320, pad 420, pad 520, or pad 620. The drape 1022 may include or correspond to drape 122, drape 222, drape 322, drape 422, drape 522, or drape 622. In some implementations, the pad 1020 and the drape 1022 are separate, and in other implementations, the pad 1020 and the drape 1022 are coupled together by LSA, such as LSA, i.e., as in a pre-packaged dressing. When the pad 1020 and the drape 1022, the LSA may be provided separately, such as in a tub of LSA.

In some implementations, kit 1000 further includes therapy device 1010. Therapy device 1010 may include or correspond to therapy device 102, 202, 302, 402, 502, or 602. In some implementations, kit 1000 may include controller 1014 including or corresponding to processor 114 and/or remote device 106, as described herein with reference to FIG. 1. Controller 1014 is configured to control operations of therapy device 102.

In some implementations, kit 1000 includes a light device 1028. The light device 1028 may include or correspond to light source (e.g., light device) 128, 228, 328, 428, 528, or 628. Additionally, or alternatively, kit 1000 further includes an additional light device (e.g., a second light device), one or more additional components 1016, or a combination thereof. The one or more additional components 1016 may include or correspond to LSA, an LSA applicator, gloves, antiseptic, medical adhesive, and/or other components.

In some implementations, kit 1000 may include a package 1002. For example, package 1002 may include a box, a bag, a container, or the like. Package 1002 may include the pad 1020 and/or the drape 1022, in addition to the one or more optional components described above. In some implementations, package 1002 may include a packaging medium (e.g., packaging material), such as foam, paper, or the like. Thus, FIG. 10 describes kit 1000 for a therapy device including a two-piece dressing with LSA.

The above specification and examples provide a complete description of the structure and use of illustrative examples. Although certain aspects have been described above with a certain degree of particularity, or with reference to one or more individual examples, those skilled in the art could make numerous alterations to aspects of the present disclosure without departing from the scope of the present disclosure. As such, the various illustrative examples of the methods and systems are not intended to be limited to the particular forms disclosed. Rather, they include all modifications and alternatives falling within the scope of the claims, and implementations other than the ones shown may include some or all of the features of the depicted examples. For example, elements may be omitted or combined as a unitary structure, connections may be substituted, or both. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one example or may relate to several examples. Accordingly, no single implementation described herein should be construed as limiting and implementations of the disclosure may be suitably combined without departing from the teachings of the disclosure.

The previous description of the disclosed implementations is provided to enable a person skilled in the art to make or use the disclosed implementations. Various modifications to these implementations will be readily apparent to those skilled in the art, and the principles defined herein may be applied to other implementations without departing from the scope of the disclosure. Thus, the present disclosure is not intended to be limited to the implementations shown herein but is to be accorded the widest scope possible consistent with the principles and novel features as defined by the following claims. The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A wound dressing comprising: a drape including a first light switchable adhesive; and a pad comprising: a second light switchable adhesive configured to couple the pad to the drape, the first light switchable adhesive and the second light switchable adhesive being different; and a light source incorporated in the pad configured to emit light and activate at least the second light switchable adhesive.

2. The wound dressing of claim 1, further comprising one or more electronic communication devices disposed on the drape or the pad.

3. The wound dressing of claim 2, wherein the one or more electronic communication devices comprise an antenna, an inductor, a printed circuit board (PCB), a near-field communication (NFC) circuit, or a Bluetooth low energy (BLE) circuit.

4. The wound dressing of claim 3, wherein the one or more electronic communication devices are configured to wirelessly communicate with a remote device or a therapy device to enable activation of the light source.

5. The wound dressing of claim 1, further comprising a power source, the power source coupled to the drape or the pad.

6. The wound dressing of claim 5, wherein the power source is configured to be coupled to the light source to enable delivery of the light to the first light switchable adhesive and the second light switchable adhesive.

7. The wound dressing of claim 1, wherein the first and the second light switchable adhesives comprise:

one or more polymers; and photo initiators configured to cause the one or more polymers to cross-link responsive to receiving the light.

8. The wound dressing of claim 7, wherein the photo initiators have a peak absorbance between 200 nanometers (nm) to 400 nm or between 750 nm to 860 nm.

9. The wound dressing of claim 1, further comprising a shroud coupled to an exterior surface of the drape of the wound dressing, the shroud configured to reflect the light within the wound dressing, block second light from entering the wound dressing, or both.

10. The wound dressing of claim 1, wherein the pad further comprises an activator configured to activate the light source.

11. A wound dressing comprising: a drape including a first light switchable adhesive configured to couple the drape to a tissue site; and a pad configured to be coupled to the drape and to a light source, the pad including a second light switchable adhesive configured to couple the pad to the drape, wherein: the light source is incorporated in the pad and is configured to emit light to activate at least the second light switchable adhesive to decouple the pad from the drape;

and while the pad is coupled to the light source and decoupled from the drape, the pad is configured to direct the light and is moveable relative to the drape to activate the first light switchable adhesive to decouple the drape from the tissue site.

12. The wound dressing of claim 11, further comprising a tube coupled to the pad, the tube configured to deliver light from the light source.

13. The wound dressing of claim 12, wherein the light source is included in or on a connector of the tube.

14. The wound dressing of claim 12, further comprising a therapy device coupled to the tube and configured to activate the light source, the therapy device including the light source.

15. The wound dressing of claim 11, further comprising a cover film removably coupled to the first light switchable adhesive.

16. The wound dressing of claim 11, wherein the first and second light switchable adhesive includes photo initiators configured to absorb or react with UV light, visible light, or both.

17. The wound dressing of claim 11, wherein the first or second light switchable adhesives comprise a dual light switchable adhesive.

18. A therapy system comprising: a wound dressing comprising: a drape including a first light switchable adhesive; a pad including a second light switchable adhesive configured to couple the pad to the drape; a light source incorporated in the pad configured to emit light and activate at least the second light switchable adhesive; and an absorbent material; and a therapy device configured to couple to the wound dressing and configured to activate the light source;

wherein the light source is configured to activate the first light switchable adhesive and the second light switchable adhesive.

19. The therapy system of claim 18, further comprising tubing configured to couple the therapy device to the wound dressing.

20. The therapy system of claim 18, further comprising a remote device in communication with the therapy device or the light source, the remote device configured to cause the therapy device to activate the light source of the wound dressing.

21. The therapy system of claim 18, wherein the therapy device comprises a controller configured to control operation of the therapy device, the light source, or both.

* * * * *